United States Patent [19]

Newton et al.

[11] Patent Number: 5,595,890
[45] Date of Patent: * Jan. 21, 1997

[54] METHOD OF DETECTING NUCLEOTIDE SEQUENCES

[75] Inventors: Clive R. Newton, Wincham; Alexander F. Markham, Crewe, both of United Kingdom

[73] Assignee: Zeneca Limited, London, England

[ * ] Notice: The term of this patent shall not extend beyond the expiration date of Pat. No. 5,137,806.

[21] Appl. No.: 390,939

[22] Filed: Feb. 17, 1995

Related U.S. Application Data

[63] Continuation of Ser. No. 13,991, Feb. 5, 1993, abandoned, which is a continuation of Ser. No. 320,550, Mar. 8, 1989, abandoned.

[30] Foreign Application Priority Data

Mar. 10, 1988 [GB] United Kingdom .................. 8805692
Jun. 15, 1988 [GB] United Kingdom .................. 8814170

[51] Int. Cl.$^6$ .............................. C12P 19/34; C12Q 1/68; C07H 21/04
[52] U.S. Cl. .......................... 435/91.2; 435/6; 536/24.3; 536/24.33
[58] Field of Search ...................... 435/6, 91.2; 536/24.3, 536/24.33

[56] References Cited

U.S. PATENT DOCUMENTS

| | | | |
|---|---|---|---|
| 4,683,195 | 7/1987 | Mullis et al. ................................. | 435/6 |
| 4,683,202 | 7/1987 | Mullis ........................................ | 435/91 |
| 4,851,331 | 7/1989 | Vary et al. ................................... | 435/6 |
| 5,137,806 | 8/1992 | LeMaistre et al. .......................... | 435/6 |

FOREIGN PATENT DOCUMENTS

| | | | |
|---|---|---|---|
| 0237362 | 9/1987 | European Pat. Off. . | |
| 0246864 | 11/1987 | European Pat. Off. . | |
| 0123513 | 2/1988 | European Pat. Off. . | |
| 0288299 | 10/1988 | European Pat. Off. . | |
| 0300796 | 1/1989 | European Pat. Off. . | |
| 0317239 | 5/1989 | European Pat. Off. . | |
| 0388171 | 3/1990 | European Pat. Off. | C12Q 1/68 |
| 0364255 | 4/1990 | European Pat. Off. . | |
| 0393743 | 10/1990 | European Pat. Off. | C12Q 1/68 |
| 8910414 | 2/1989 | WIPO . | |
| 8909285 | 10/1989 | WIPO . | |
| 9011372 | 4/1990 | WIPO . | |
| 92/15712 | 9/1992 | WIPO . | |

OTHER PUBLICATIONS

S. J. Dermer et al, Labroatory Investigation, 1988, 59, (3), 403–408.
F. Panabieres et al, Gene, 1982, 19, 321–326.
L. A. Wrischnik et al, Nucleic Acids Research, 1987, 15, 2, 529–542.
J. L. Bos et al, Nature, 1987, 327, 293–297.
H. A. Ehrlich, Nature 1988, 331, 461–462.
R. K. Saiki et al, Science, 1985, 230, 1350–1354.
M. S. Lee et al, Science, 1987, 237, 175–178.
Journal of Cellular Biochemistry, supp/13E, 3rd–24th Apr. 1989, Abstract No. WH001, p.270 A. R. Liss.
D. R. Engelke et al., P.N.A.S., 1988, 85, 544–548.
Reckman et al, "The elongation of mismatched primers by DNA polymerase α from calf thymus", Nucleic Acids Research 11(20):7251–7260 (1983).
Winnacker, "From genes to clones: introduction to gene technology", pp. 41–42 (1987).
Li et al, "Amplification and analysis of DNA sequences in single human sperm and diploid cells", Nature 335:414–417 (1988).
Tindall et al, "Fidelity of DNA Synthesis by the *Thermus aquaticus* DNA Polymerase", Biochemistry 27:6008–6013 (1988).
Kunkel et al, "Exonucleolytic proofreading by calf thymus DNA polymerase δ", Proc. Natl. Acad. Sci. USA 84:4865–4869 (1987).
Newton et al, "Diagnosis of $\alpha_1$–antitrypsin deficiency by enzymatic amplification of human genomic DNA and direct sequencing of polymerase chain reaction products", Nucleic Acids Research 16(7):8233–8242.
Newton et al, "Analysis of any point mutation in DNA. The amplification refractory mutation system (ARMS)", Nucleic Acids Research 17(7):2503–2516 (1989).
McMahon et al, "Characterization of c–Ki–ras oncogene alleles by direct sequencing of enzymatically amplified DNA from carcinogen–induced tumors", Proc. Natl. Acad. Sci. USA 84:4974–4978 (1987).
Dermer and Johnson, Methods in Laboratory Investigation, "Rapid DNA Analysis of $\alpha_1$–Antitrypsin Deficiency: Application of an Improved Method for Amplifying Mutated Gene Sequences", Laboratory Investigation 59(3):403–408 (1988).
Gibbs et al, "The Polymerase Chain Reaction: Methodology and Applications", J. Cellular Biochemistry, Suppl. 13E (Apr. 1989).
Fisher and Korn, "DNA Polymerase–α, Purif. and Struct. Charact. of the Near Homogenous Enz. from Hum. KB Cells", The Journal of Biological Chemistry 252(18):6528–6535 (1977).
Fisher and Korn, "Enzymological Characterization of KB Cell DNA Polymerase–α, II. Specificity of the Protein–Nucleic Acid Interaction", The Journal of Biological Chemistry 254(21):11033–11039 (1979).

(List continued on next page.)

*Primary Examiner*—George C. Elliott
*Assistant Examiner*—John S. Brusca
*Attorney, Agent, or Firm*—Nixon & Vanderhye P.C.

[57] ABSTRACT

The present invention relates to a method for detecting the presence or absence of one or more variant nucleotide sequences. The method comprises (i) contacting a nucleic acid sample with a diagnostic primer which is substantially complementary to a diagnostic portion of a target base sequence, whereby extension of the diagnostic primer on a target template under appropriate conditions is only achieved where a terminal nucleotide of the diagnostic primer is complementary to either a suspected variant nucleotide or a corresponding normal nucleotide of the target base sequence, and (ii) detecting the presence or absence of an extension product. Kits for performing diagnostic tests are also disclosed.

11 Claims, 8 Drawing Sheets

OTHER PUBLICATIONS

Fisher and Korn, "Enzymological Characterization of KB Cell DNA Polymerase–α, III. The Polymerization Reaction With Single–Stranded DNA", The Journal of Biological Chemistry 254(21):11040–11046 (1979).

Fisher et al, "Enzymological Characterization of DNA Polymerase α, Bas. Cat. Prop., Proc, and Gap Util. of the Homol. Enz. from Human KB Cells", The Journal of Biological Chemistry 254(13):6128–6137 (1979).

Fisher and Korn, "Ordered Sequential Mechanism of Substrate Recognition and Binding by KB Cell DNA Polymerase α", Biochemistry 20(16):4560–4569 (1981).

Fisher and Korn, "Properties of the Primer–Binding Site and the Role of Magnesium Ion in Primer–Template Recognition by KB Cell DNA Polymerase α" Biochemistry 20(16):4570–4578 (1981).

Kornberg "DNA Replication", W. H. Freeman & Co./San Francisco, Chapter 3 (1980), p. 96.

Orkin et al, "Direct Detection of the Common Mediterranean β–Thalassemia Gene with Synthetic DNA Probes", J. Clin. Invest. 71:775–779 (Mar. 1983).

Wallace et al, "Application of synthetic oligonucleotides to the diagnosis of human genetic diseases" Biochimie 67:755–762 (1985).

Saiki et al, "Analysis of enzymatically amplified β–globin and HLA–DQα DNA with allele-specific oligonucleotide probes", Nature 324:163–166 (1986).

Embury et al, "Rapid Prenatal Diagnosis of Sickle Cell Anemia by a New Method of DNA Analysis", The New England Journal of Medicine 316(11):656–661 (1987).

Aboul–ela et al, "Base–base mismatches. Thermodynamics of double helix formation for $dCA_3XA_3G + dCT_3YT_3G$ (X, Y=A,C,G,T)", Nucleic Acids Research 13(13):1200 (1985).

Boosalis et al, "DNA Polymerase Insertion Fidelity", The Journal of Biological Chemistry 262(30):14689–14696 (1987).

Mullis and Faloona, "[21] Specific Synthesis of DNA in Vitro via a Polymerase–Catalyzed Chain Reaction" Polymerase Chain Reaction, Methods in Enzymology 155:335–351 (1987).

Okayama et al, "Rapid, nonradioactive detection of mutations in the human genome by allele-specific amplification", J. Lab. Clin. Med. 114(2):105–113 (1989).

Chebab et al, "Detection of Sickle Cell anaemia and thalassaemias", Nature 329:293–294 (1987).

Chebab et al, "Amer. Soc. of Hematol. 29th Ann. Meet.", American Society of Haematology (Dec. 5–8, 1987), Rapid and non–radioactive method for the Dect. of β–Thalassemia mutations: application to two common mutations, Abstract No. 145.

Chebab and Kan, "Detection of specific DNA sequences by fluorescence amplification: A color complementation assay", Proc. Natl. Acad. Sci. USA 86:9178–9182 (1989).

Gyllensten and Erlich, "Generation of single–stranded DNA by the polymerase chain reaction and its application to direct sequencing of the HLA–DQA locus", Proc. Natl. Acad. Sci. USA 85:7652–7656 (1988).

Petruska et al, "Comparison of nucleotide interactions in water, proteins, and vacuum: Model for DNA polymerase fidelity", Proc. Natl. Acad. Sci. USA 83:1559–1562 (1986).

Petruska et al, "Comparison between DNA melting thermodynamics and DNA polymerase fidelity", Proc. Natl. Acad. Sci. USA 85:6252–6256 (1988).

Ou et al, "DNA Amplification for direct Detection of HIV–1 in DNA of Peripheral Blood Mononuclear Cells", Science 239:295–297 (1988).

Kowk et al, "Enzymatic Amplification of HTLV–I Viral Sequences From Peripheral Blood Mononuclear Cells and Infected Tissues", Blood 72(4):1117–1123 (1988).

Saiki et al, "Primer–directed Enzymatic Amplification of DNA with a Thermostable DNA Polymerase", Science 239:487–491 (1988).

Kazazian, "Use of PCR in the Diganosis of Monogenic Disease", Chapter 14, PCR Technology (HA Ehrlich Ed) Stockton Press–NY, p. 153 (1989).

Ng et al, "Recognition and Binding of Template–Primers Containing Defined Abasic Sites by Drosophila DNA Polymerase α Holoenzyme", The Journal of Biological Chemistry 264(22):13018–13023 (1989).

Kwok et al, "Effects of primer–template mismatches on the polymerase chain reaction: Human immunodeficiency virus type 1 model studies", Nucleic Acids Research 18(4):999–1005 (1990).

Mendelman et al, "Base Mispair Extension Kinetics", The Journal of Biological Chemistry 265(4):2338–2346 (1990).

Weiss and Fisher, "Interaction of Drosophila DNA Polymerase α Holoenzyme with Synthetic Template–Primers Containing Mismatched Primer Bases or Propanodeoxyguanosine Adducts at Various Positions in Template and Primer Regions", The Journal of Biological Chemistry 267(26):18520–18526 (1992).

Erlich et al, "Specific DNA amplification", Nature 331:461–462 (1988).

Kazazian et al, J. Lab. Clin. Med., 1989, 114 (2), 95–96.

Ehrlich et al, Current Communications in Molecular Biology, A Banbury Center Meeting—Polymerase Chain Reaction, 1989.

Wu et al, P.N.A.S., 86, 1989, 2757–2760.

Gibbs et al, Nucleic Acids Research, 1989, 17 (7), 2437–2448.

Hejtmancik et al, Lancet, 1986/Oct., 767–769.

OR

METHOD OF DETECTING NUCLEOTIDE SEQUENCES

This is a continuation of application Ser. No. 08/013,991, filed Feb. 5, 1993, now abandoned; which is a continuation of 07/320,550, filed Mar. 8, 1989, now abandoned.

The present invention relates to a method for detecting the presence or absence of one or more variant nucleotide sequences by amplification or the absence thereof and kits therefor.

The present invention is of particular interest in the diagnostic screening of DNA samples for inherited conditions, predispositions or somatic mutations and provides inter alia a general method for the facile detection of point mutations. It is also useful in the detection and typing of infectious pathogens by analysis of their DNA or RNA.

Several hundred genetic diseases are known to exist in man which result from particular mutations at the DNA level. The molecular basis for certain of these diseases is already known and research is rapidly revealing the molecular basis for those genetic diseases for which the nature of the mutation is at present unknown. Where the precise molecular basis for the inherited condition is not known, diagnosis of the disorder or location of carriers may be provided in informative pedigrees by RFLP technology using DNA probes in genetic linkage with the disease locus. Thus, at present Duchenne Muscular Dystrophy, Cystic Fibrosis and Huntington's Chorea inter alia may for example be diagnosed using RFLP technology. Such testing however needs to be performed separately in respect of each condition and a substantial amount of work is required, each case requiring inter alia DNA purification, restriction enzyme digestion, agarose gel electrophoresis, Southern blotting, hybridisation, detection of hybridised gene probe and pedigree analysis. Certain other inherited conditions are known to be associated with single point mutations in genes, but each of these conditions must be analysed separately and further particular difficulties arise where the point mutations are heterogeneous. Thus for example more than 40 different point mutations can cause β-thalassaemia and at least 5, and probably many more than 12, point mutations can cause hemophilia A. In respect of these heterogeneous conditions, each potential mutation point may need at present to be analysed separately. This can involve complex RFLP haplotype analysis with multiple restriction enzymes.

A number of point mutations in somatic cells have been implicated in the development of various cancers for example point mutations within the ras oncogene (J. L. Boos et al, *Nature* 327,293 (1987).

European Patent Application No. 87302196.8 (Publication No 237,362) of Cetus Corporation describes a process for detecting the presence or absence of at least one nucleotide variation in sequence in one or more nucleic acids contained in a sample, which process comprises:

(a) treating the sample, together or sequentially with four different nucleotide triphosphates, an agent for polymerization of the nucleotide triphosphates, and one oligonucleotide primer for each strand of each nucleic acid suspected of containing said variation under hybridizing conditions, such that for each nucleic acid strand containing each different variation to be detected, an extension product of each primer is synthesized which is complementary to each nucleic acid strand, wherein said primer or primers are selected so as to be substantially complementary to each nucleic acid strand containing each different variation, such that the extension product synthesized from one primer, when it is separated from its complement, can serve as a template for synthesis of the extension product of the other primer;

(b) treating the sample under denaturing conditions to separate the primer extension products from their templates if the variation(s) to be detected are present;

(c) treating the sample, together or sequentially, with said four nucleotide triphosphates, an agent for polymerization of the nucleotide triphosphates, and oligonucleotide primers such that a primer extension product is synthesized using each of the single strands produced in step (b) as a template, wherein steps (b) and (c) are repeated a sufficient number of times to result in detectable amplification of the nucleic acid containing the sequence variation(s), if present;

(d) affixing the product of step (c) to a membrane;

(e) treating the membrane under hybridization conditions with a labeled sequence-specific oligonucleotide probe capable of hybridizing with the amplified nucleic acid sequence only if a sequence of the probe is complementary to a region of the amplified sequence; and (f) detecting whether the probe has hybridized to an amplified sequence in the nucleic acid sample.

The detection of the presence or absence of at least one nucleotide variation may in certain special situations, be achievable by different techniques. Thus in the unusual cases where the point mutation creates or destroys a restriction site (for example sickle cell anemia), restriction enzyme digestion may be employed either before or after amplification [F. F. Chehab et al *Nature* 329, 293, (1987)]. Moreover in respect of large deleted nucleic acid sequences primers for amplification may be prepared for regions within the suspected deletion such as the 23 kb deletion causing α-thalassaemia; in such cases failure to amplify the deleted sequence confirms the deletion and thus for example is diagnostic of α-thalassaemia [F. F. Chehab et al, *Nature* 329,293 (1987)].

The amplification process of European Patent Publication No. 237,362 provides certain advantages over RFLP (restriction fragment length polymorphism) and allele specific oligonucleotide techniques as described for example by Kan and Dozy, Proceedings of the National Academy of Sciences (USA) 75, 5631 (1978), Rubin and Kan, *Lancet*, 1985-I,75(1985), Conner et al, Proceedings of the National Academy of Sciences (USA), 80, 78 (1983), Kidd et al., *Nature*, 304, 230 (1983) and Piratsu et al., New England Journal of Medicine, 309, 284 (1983).

Nevertheless the European Patent Publication No. 237, 362 describes a process which involves the indiscriminate amplification of a particular sequence of interest which inevitably results in the need for a number of time-consuming further detection steps involving either the further use of a labelled sequence-specific oligonucleotide probe which may need to be capable of distinguishing between sequences differing by as little as a single nucleotide and/or the use of a specific restriction endonuclease in those limited cases where the point mutation of interest creates or destroys the enzyme recognition sequence and/or use of direct sequencing methods on the amplified DNA [see C. Wong et al *Nature* 330, 384 (1987].

There is a need for a simple method for directly detecting at least one single base difference in nucleic acids such as genomic DNA in which detection steps are minimised resulting in a method which may be performed quickly, accurately and easily with minimal operator skill.

The present invention is based on the discovery that by selecting the nucleotide sequence of an oligonucleotide primer appropriately it is possible to selectively achieve primer extension of either a sequence containing a suspected variant nucleotide or the corresponding sequence containing the normal nucleotide or to prevent such primer extension thus substantially simplifying the detection procedures necessary.

According to one feature of the present invention there is provided a method for detecting the presence or absence of at least one variant nucleotide in one or more nucleic acids contained in a sample, which method comprises:

treating the sample, together or sequentially with appropriate nucleoside triphosphates, an agent for polymerisation of the nucleoside triphosphates and a diagnostic primer for a diagnostic portion of a target base sequence under hybridising conditions, the nucleotide sequence of the said diagnostic primer being such that it is substantially complementary to the said diagnostic portion, a terminal nucleotide of the diagnostic primer being either complementary to the suspected variant nucleotide or to the corresponding normal nucleotide, whereby an extension product of the diagnostic primer is synthesised when the said terminal nucleotide of the diagnostic primer is complementary to the corresponding nucleotide in the target base sequence, no extension product being synthesised when the said terminal nucleotide of the diagnostic primer is not complementary to the corresponding nucleotide in the target base sequence; and detecting the presence or absence of the suspected variant nucleotide from the presence or absence of an extension product.

It should be appreciated that whilst the method of the present invention is of particular interest in detecting the presence or absence of point mutations, the method is equally applicable to detecting the presence or absence of deletions, including deletions of more than one nucleotide as well as to detecting the presence or absence of substitutions of more than one nucleotide. In this regard it is simply necessary to know the relevant nucleotides, especially the relevant terminal nucleotide, so that the necessary diagnostic primer(s) may be designed appropriately.

It will be appreciated that any extension product formed may be detected in any convenient form, for example in single or double-stranded form.

It will further be appreciated that any extension product obtained may if desired be amplified by the polymerase chain reaction (PCR) as described in U.S. Pat. Nos. 4,683,195 and 4,683,202, by the use of Q-beta replicase as described in PCT Patent Publication WO87/06270 and in Biotechnology Vol.6 October 1988, by the use of the transcription based nucleic acid amplification of Siska Corporation as described in PCT Patent Publication WO88/10315, or by the use of linear amplification. In this connection the expression "linear amplification" is used herein to refer to amplification using a single primer for each diagnostic portion in the presence of an agent for polymerisation and appropriate nucleotide triphosphates whereby amplification is effected by primer extension based on the use of a single strand of sample nucleic acid as template.

In a first and especially preferred embodiment of the present invention the method comprises:

1) treating the sample, together or sequentially, with appropriate nucleoside triphosphates, an agent for polymerisation of the nucleoside triphosphates a diagnostic primer for a diagnostic portion of a target base sequence and a corresponding amplification primer under hybridising conditions, the nucleotide sequence of the said diagnostic primer being such that it is substantially complementary to the said diagnostic portion, a terminal nucleotide of the diagnostic primer being either complementary to the suspected variant nucleotide or to the corresponding normal nucleotide, whereby an extension product of the diagnostic primer is synthesised when the said terminal nucleotide of the diagnostic primer is complementary to the corresponding nucleotide in the target base sequence, no extension product being synthesised when the said terminal nucleotide of the diagnostic primer is not complementary to the corresponding nucleotide in the target base sequence; any extension product of the diagnostic primer formed being capable of serving as a template for synthesis of an extension product of the said amplification primer after separation from its complement;

2) treating the sample under denaturing conditions to separate the primer extension product from its template where such extension product is formed;

3) contacting single strands produced in step (2), either together or sequentially, with appropriate nucleoside triphosphates, an agent for polymerisation of the nucleoside triphosphates, a diagnostic primer and an amplification primer as herein defined whereby, where possible, to synthesise further extension products using the single strands produced in step (2) as templates.

4) repeating steps (2) and (3) a sufficient number of times to result in detectable amplification of the appropriate nucleotide sequence; and 5) detecting the presence or absence of the suspected variant nucleotide from the presence or absence of an amplification product obtained in step (4).

In a second embodiment of the present invention the said sample is treated, together or sequentially with either (a) a first diagnostic primer having a sequence substantially complementary to a diagnostic portion of a first nucleic acid sequence, the first diagnostic primer having a terminal nucleotide complementary to the said suspected variant nucleotide, and a second diagnostic primer having a sequence substantially complementary to a diagnostic portion of a second nucleic acid sequence, the second diagnostic primer having a terminal nucleotide complementary to the complementary suspected variant nucleotide; or (b) a first diagnostic primer having a sequence substantially complementary to a diagnostic portion of a first nucleic acid sequence, the first diagnostic primer having a terminal nucleotide complementary to the normal nucleotide which corresponds to the said suspected variant nucleotide, and a second diagnostic primer having a sequence substantially complementary to a diagnostic portion of a second nucleic acid sequence, the second diagnostic primer having a terminal nucleotide complementary to the normal nucleotide which corresponds to the said suspected variant nucleotide;

the said terminal nucleotide of the first diagnostic primer and the said terminal nucleotide of the second diagnostic primer being either both at the 5' end or both at the 3' end of the respective primers and the first nucleic acid sequence being in the opposite sense to the second nucleic acid sequence.

In this embodiment therefore, the second diagnostic primer may be considered to be an amplification primer as referred to above and hereinafter.

This second embodiment may enable discrimination and specificity to be increased since any artefactual product requires priming to occur at the relevant terminal end (generally the 3'-terminal end) of two mis-matched oligonucleotides rather than at a single end as is the case where only a single diagnostic primer is used.

Detection of the presence or absence of a suspected variant nucleotide may be effected for example as described hereinafter.

In a third embodiment of the present invention a sample comprising DNA containing a suspected variant nucleotide is subjected to amplification, for example by linear amplification as herein defined or, for example as described in U.S. Pat. Nos.4,683,195 and 4,683,202, in PCT Patent Publication WO87/06270, in Biotechnology Vol.6, October 1988 or in PCT Patent Publication WO88/10315 and the amplification product treated with a diagnostic primer for a diagnostic portion of a target base sequence under hybridising conditions, in the presence of appropriate nucleoside triphosphates, and an agent for polymerisation of the nucleoside triphosphates, the nucleotide sequence of the said diagnostic primer being such that it is substantially complementary to the said diagnostic portion, a terminal nucleotide of the diagnostic primer being either complementary to the suspected variant nucleotide or to the corresponding normal nucleotide.

Thus in this third embodiment of the invention conventional amplification may be performed in the desired number of cycles and hybridisation with the diagnostic primer attempted as the next step prior to the detection step. No amplification primer need be employed.

This third embodiment is of interest since the quantity of the agent(s) for polymerisation required may be substantially reduced (for example at least halved) as indeed may the quantity of the nucleoside triphosphates used and the number of Polymerase Chain Reaction (PCR) heater machines employed. This third embodiment thus enables substantial cost savings to be achieved. Moreover since the amplification step may be effected at a range of convenient temperatures without disadvantage this third embodiment only requires that the more temperature sensitive attempted hybridisation with the diagnostic probe to be effected once, thus reducing still further the risk of false priming of a terminal mismatched (generally 3'-mismatched) diagnostic primer. This third embodiment thus provides a potentially more reliable and robust method for the non-expert to use, which is more forgiving of operator error. This third embodiment further obviates the desire for an extra polymerase chain reaction control step since the initial amplification provides its own internal control.

If desired the diagnostic primer may carry a signal or label which would not be at risk of destruction, for example in a high temperature cycling technique such as PCR. For example labelling may be effected using an appropriate labelling or signalling moiety, such as alkaline phosphatase or horseradish peroxidase as described.

In this regard the application of thermostable enzymes for labelling such as a phosphatase derived from *Thermus aquaticus*, may be of interest.

A fourth and preferred embodiment of the present invention modifies the third embodiment of the present invention by introducing the feature of using two diagnostic primers as described in the second embodiment of the present invention, the second diagnostic primer potentially serving as an amplification primer.

Thus in the fourth embodiment of the present invention a sample comprising DNA containing a suspected variant nucleotide is subjected to amplification and the amplified product treated, together or sequentially, with either:

(a) a first diagnostic primer having a sequence substantially complementary to a diagnostic portion of a first nucleic acid sequence, the first diagnostic primer having a terminal nucleotide complementary to the said suspected variant nucleotide, and a second diagnostic primer having a sequence substantially complementary to a diagnostic portion of a second nucleic acid sequence, the second diagnostic primer having a terminal nucleotide complementary to the nucleotide which is complementary to the said, suspected variant nucleotide, or (b) a first diagnostic primer having a sequence substantially complementary to a diagnostic portion of a first nucleic acid sequence, the first diagnostic primer having a terminal nucleotide complementary to the normal nucleotide which corresponds to the said suspected variant nucleotide, and a second diagnostic primer having a sequence substantially complementary to a diagnostic portion of a second nucleic acid sequence, the second diagnostic primer having a terminal nucleotide complementary to the nucleotide which is complementary to the said normal nucleotide which corresponds to the said suspected variant nucleotide;

the said terminal nucleotide of the first diagnostic primer and the said terminal nucleotide of the second diagnostic primer being either both at the 5' end or both at the 3' end of the respective primers and the first nucleic acid sequence being complementary to the second nucleic acid sequence.

In general the said terminal nucleotide of the first diagnostic primer and the said terminal nucleotide of the second diagnostic primer are each at the 3' end of their respective primers.

The fourth embodiment of the present invention thus combines the potential advantages of the above-defined second and third embodiments of the invention, these being inter alia a potentially increased specificity, reduced cost and a more robust user-friendly technique.

Detection of the presence or absence of a suspected variant nucleotide may be effected for example as described hereinafter.

It will be appreciated that the amplified product once treated with either (a) or (b) as hereinbefore defined may be subjected to one or more final cycles as desired. Where multiple cycles are effected then a further product may be obtained, this being a hybrid of the extension products of the diagnostic primers. The various products will be formed in ratios depending on the relative ratios of the original PCR (polymerase chain reaction) primer oligonucleotides and the added diagnostic primer oligonucleotides.

Where amplification is effected either by the use of diagnostic and amplification primers or by the use of two diagnostic primers for example as described in the first and second embodiments of the present invention or as part of the amplification procedure described in European Patent Publication No. 237,362, the steps of (a) denaturing to separate primer extension products from their template and (b) contacting single strands thereby obtained, either together or sequentially, with appropriate nucleoside triphosphates, an agent for polymerisation of the nucleoside triphosphates, and the relevant primers to synthesise further extension products; are preferably repeated at least five times (cycles) up to an indefinite number, especially where the primer is refractory to amplification, without detriment to the present invention. More preferably 15–60 eg. 15–30 times (cycles) are employed if the sample contains human genomic DNA. If the sample comprises cells, preferably they are heated before step (a) to expose the nucleic acids therein to the reagents. This step avoids purification of the nucleic acids prior to reagent addition. In this regard, it will be appreciated that the present invention represents a substantial improvement over prior processes even if DNA purification from a sample is performed prior to the attempted amplification.

It will be appreciated that in step (b) contact between the single strands produced in step (a) and the appropriate nucleoside triphosphates, an agent for polymerisation of the nucleoside triphosphates, the primer(s), for example the diagnostic primer(s) and/or the amplification primer(s) may be effected either by addition of these materials to the reaction mixture following separation of the primer extension product from its template (step a) or reliance may be placed on the materials already present in the reaction mixture. Indeed any one or more different nucleoside triphosphates and/or the agent for polymerisation and/or the primer(s), for example the diagnostic primer(s) and/or the amplification primer may be added at any stage of the process of the invention.

According to a fifth and preferred embodiment of the present invention there is provided a method as hereinbefore defined in which amplification is effected by primer extension based on the use of a single strand of sample nucleic acid as template.

Thus in this embodiment primer extension is effected based on the use of the same strand of sample nucleic acid as template, no amplification primer being present. Thus amplification is arithmetic rather than exponential, exponential amplification being achievable, at least in theory, with the polymerase claim reactions (PCR). The advantage of this fifth embodiment of the present invention (also referred to herein as linear amplification) is that artefactual products if produced cannot themselves be subjected to exponential amplification.

Linear amplification may be effected by any convenient means and thus may be effected by the use of complementary nucleoside triphosphates in the presence of an agent for polymerisation of the nucleoside triphosphates to produce primer extension products of indeterminate length where a sufficient degree of complementarity is present between the diagnostic primer and the sample nucleic acid. Preferably where all complementary nucleoside triphosphates are to be employed the sample nucleic acid is subjected to endonuclease digestion, the restriction endonuclease being selected so as to ensure that cleavage of the sample nucleic acid is effected at a site adequate to permit the formation of primer extension products of fixed length. Advantageously, however, the linear amplification may be effected in the presence of only 1, advantageously only 2 or preferably only 3 nucleoside triphosphates such that the diagnostic primer in its bound state (ie hybridised to the sample nucleic acid) can only extend as far as the presence of only the 1, 2 or 3 nucleoside triphosphates will permit. Once a nucleoside triphosphate is present in the sample nucleic acid for which no complementary nucleoside triphosphate is present, then primer extension will cease.

If desired the linear amplification may be effected at the melting temperature (Tm) of the sequence. At this temperature the diagnostic primer hybridised to the complementary sequence in the sample nucleic acid is in equilibrium with the diagnostic primer free in solution and thus the diagnostic primer (optionally in extended form) is being rapidly hybridised to and denatured from the sample nucleic acid. If desired the linear amplification may also be effected by thermal oscillation. Such thermal oscillation would generally involve rapid temperature fluctuation about the melting temperature of the sequence.

If only 1, 2 or 3 nucleoside triphosphates are present then the diagnostic primer will only extend as far as the presence of these nucleoside triphosphates will permit. As indicated above, where there is a mismatch between for example the 3' terminal end of the diagnostic primer and the corresponding nucleoside triphosphate in the sample nucleic acid no primer extension will be effected. Where, however, the 3' terminal nucleoside triphosphate is complementary with the corresponding nucleoside triphosphate in the sample nucleic acid, primer extensions will be effected.

Where only 1, 2 or 3 nucleoside triphosphates are used and in use, the terminal nucleoside triphosphate of the extended diagnostic primer is only employed once, then it may be advantageous to use a dideoxy nucleoside triphosphate as the nucleoside triphosphate which in use will constitute the terminal nucleoside triphosphate of the diagnostic primer extended product. This will assist in production of a clearly terminated extension of the diagnostic primer.

If desired one or more of the nucleoside triphosphates present in the reaction mixture for the purpose of incorporation into the extended primer(s) may be labelled or marked in any convenient manner. Thus for example one or more of the nucleoside triphosphates may be fluorescently labelled. This labelling of the nucleoside triphosphates is of particular interest in relation to the fifth embodiment of the present invention where production of an extension product of the diagnostic primer can be detected by detection of the labelled or marked nucleoside triphosphate(s) incorporated in the extension product. Where no extension product is formed no incorporation takes place, and the labelled or marked nucleoside triphosphates may for example be washed away. More particularly the fifth embodiment of the present invention avoids the problem of amplification of artefactual products and thus enables good discrimination to be achieved in the presence of the labelled or marked nucleoside triphosphate(s). Where amplification is effected for example by the use of PCR any production of an artefactual product may result in amplification of that product and thus incorporation of the labelled or marked nucleoside triphosphate thereby reducing discrimination.

In addition to the above it may be desirable that the diagnostic primer carry one member of an immunological binding pair, for example an antigen or an antibody, or one member of a complex forming pair, for example biotin, for binding to the other member of said binding pair or forming pair for the purpose of capture on to solid phase.

According to a further feature of the present invention there is provided a kit for detecting the presence or absence of at least one variant nucleotide in one or more nucleic acids contained in a sample, which kit comprises:

(1) a diagnostic primer for each diagnostic portion of a target base sequence, the nucleotide sequence of each diagnostic primer being such that it is substantially complementary to the said diagnostic portion, a terminal nucleotide of the diagnostic primer being either complementary to the suspected variant nucleotide or to the corresponding normal nucleotide such that in use an extension product of the diagnostic primer is synthesised when the said terminal nucleotide of the diagnostic primer is complementary to the corresponding nucleotide in the target base sequence, no extension product being synthesised when the said terminal nucleotide of the diagnostic primer is not complementary to the corresponding nucleotide in the target base sequence;

(2) each of four different nucleoside triphosphates; and (3) an agent for polymerisation of the nucleoside triphosphates in (2).

Advantageously the kit of the present invention additionally comprises an amplification primer corresponding to each diagnostic primer, the nucleotide sequence of the amplification primer being such that any extension product of the corresponding diagnostic primer may, after separation from its complement, serve as a template for synthesis of an extension product of the amplification primer. For example the kit of the present invention comprises either or both of the sets of diagnostic primers detailed above in relation to the second embodiment of the invention as defined above.

The kit of the present invention may also, if desired, include internal control primers, where appropriate.

It is especially preferred, however, that the kit of the present invention comprises PCR (polymerase chain reaction) primers and a diagnostic primer (as hereinafter defined) in respect of each suspected variant nucleotide. If desired the kit may additionally contain either or both of the sets of diagnostic primers detailed above in relation to the second embodiment of the invention.

Each of the materials detailed in (1), (2) and (3) and/or the amplification primer may be conveniently packaged in a separate container, but preferably all may be combined in a single container to which the material to be analysed is added. Advantageously the single container will additionally contain buffer.

It will be appreciated that where the kit of the present invention contains both sets of diagnostic primers (a) and (b) detailed above in relation to the second embodiment of the invention both sets of diagnostic primers will not be present together in a single container, although each set of primers may be present together with each of the materials detailed in (2) and (3) and/or amplification primers in separate containers. Where the sample to be tested is initially to be amplified according to European Patent Publication No. 237,362, it may be advantageous to include the PCR primers as well as the diagnostic primer(s) in a single container together with the materials in (2) and (3) above. If desired however the diagnostic primer(s) may be present in a separate container for later use after amplification has been effected.

The term "nucleoside triphosphate" is used herein to refer to nucleosides present in either DNA or RNA and thus includes nucleosides which incorporate adenine, cytosine, guanine, thymine and uracil as base, the sugar moiety being deoxyribose or ribose. In general deoxyribonucleosides will be employed in combination with a DNA polymerase. It will be appreciated however that other modified bases capable of base pairing with one of the conventional bases adenine, cytosine, guanine, thymine and uracil may be employed. Such modified bases include for example 8-azaguanine and hypoxanthine.

The term "nucleotide" as used herein can refer to nucleotides present in either DNA or RNA and thus includes nucleotides which incorporate adenine, cytosine, guanine, thymine and uracil as base, the sugar moiety being deoxyribose or ribose. It will be appreciated however that other modified bases capable of base pairing with one of the conventional bases, adenine, cytosine, guanine, thymine and uracil, may be used in the diagnostic primer and amplification primer employed in the present invention. Such modified bases include for example 8-azaguanine and hypoxanthine.

It will be appreciated that where the process of the present invention is to be used for detecting the presence or absence of a suspected variant nucleotide which is adjacent to a portion of the target base sequence which does not contain all four different nucleotides, then an extension product of the diagnostic primer and, if desired, an extension product of the amplification primer may be formed in the presence of only the appropriate corresponding nucleoside triphosphates and all four different nucleoside triphosphates would not be necessary.

The agent for polymerization of the nucleoside triphosphates may be any compound or system which will function to accomplish the synthesis of primer extension products, including enzymes. Suitable enzymes for this purpose include, for example, E. coli DNA Polymerase I, Klenow fragment of E. coli DNA polymerase I, T4 DNA polymerase, other available DNA polymerases, reverse transcriptase, and other enzymes, including thermostable enzymes. The term "thermostable enzyme" as used herein refers to an enzyme which is stable to heat and is heat resistant and catalyzes (facilitates) combination of the nucleotides in the proper manner to form the primer extension products which are complementary to each nucleic acid strand. Generally, the synthesis will be initiated at the 3' end of each primer and will proceed in the 5' direction along the template strand, until synthesis terminates, producing molecules of different lengths. There may be enzymes for example, thermostable enzymes, however, which initiate synthesis at the 5' end and proceed in the other direction, using the same process as described above. A preferred thermostable enzyme which may be employed in the process of the present invention is that which can be extracted and purified from *Thermus aquaticus*. Such enzyme has a molecular weight of about 86,000–90,000 daltons as described in European Patent Publication No. 237,362 (see also European Patent Publication No 258,017). *Thermus aquaticus* strain YT1 is available without restriction from the American Type Culture Collection, 12301 Parklawn Drive, Rockville, Md., USA as ATCC 25,104.

The expression "diagnostic portion" as used herein means that portion of the target base sequence (as hereinafter defined) which contains as its terminal nucleotide the potential variant nucleotide, the presence or absence of which is to be detected. Generally the potential variant nucleotide will be at the 5'-terminal end of the diagnostic portion since in general synthesis of primer extension products will be initiated at the 3' end of each primer as described above. Where however an agent for polymerisation is to be used which initiates synthesis at the 5' end of the diagnostic primer and proceeds in the 3' direction along the template strand until synthesis terminates the "diagnostic portion" will contain the potential variant nucleotide at its 3' end. The diagnostic primers will also be appropriately designed in this regard as set out below.

The expression "target base sequence" as used herein means a nucleotide sequence comprising at least one diagnostic portion (as hereinbefore defined). Thus for example in a single test for β-thalassaemias the target sequence may contain up to 60, for example 50 diagnostic portions, each diagnostic portion containing a single potential variant nucleotide.

The term "oligonucleotide" as used herein is defined as a molecule comprised of two or more deoxyribonucleotides or ribonucleotides, preferably more than three. Its exact size will depend on many factors, such as the reaction temperature, salt concentration, the presence of formamide and the presence of other close mutation(s), such as in sickle cell Hb C disease, which in turn depend on the ultimate function or use of the oligonucleotide. Indeed, the exact sequence of the oligonucleotide may also depend on a number of factors as described hereinafter. The oligonucleotide may be derived synthetically or by cloning.

The term "primer" as used herein refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, i.e., in the presence of appropriate nucleoside triphosphates and an agent for polymerisation such as DNA polymerase in an appropriate buffer ("buffer" includes pH, ionic strength, cofactors, etc.) and at a suitable temperature.

The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the agent for polymerization. The exact lengths of the primers will depend on many factors, including temperature and source of primer and use of the method. For example, depending on the complexity of the target sequence, the diagnostic and amplification primers typically contain 12–35, for example, 15–35 nucleotides, although they may contain more or fewer nucleotides. Short primer molecules generally require lower temperatures to form sufficiently stable hybrid complexes with the template.

The term "complementary to" is used herein in relation to nucleotides to mean a nucleotide which will base pair with another specific nucleotide. Thus adenosine triphosphate is complementary to uridine triphosphate or thymidine triphosphate and guanosine triphosphate is complementary to cytidine triphosphate. It is appreciated that whilst thymidine triphosphate and guanosine triphosphate may base pair under certain circumstances they are not regarded as complementary for the purposes of this specification. It will also be appreciated that whilst cytosine triphosphate and adenosine triphosphate may base pair under certain circumstances they are not regarded as complementary for the purposes of this specification. The same applies to cytosine triphosphate and uracil triphosphate.

The primers herein are selected to be "substantially" complementary to the different strands of each specific sequence to be amplified. This means that the primers must be sufficiently complementary to hybridize with their respective strands. Therefore, the primer sequence need not reflect the exact sequence of the template. For example, where the diagnostic primer comprises a nucleotide sequence in which the 3'-terminal nucleotide is complementary to either the suspected variant nucleotide or the corresponding normal nucleotide a non-complementary nucleotide fragment may be attached to the 5'-end of the primer, with the remainder of the primer sequence being complementary to the diagnostic portion of the target base sequence. Commonly, however, the primers have exact complementarity except in so far as non-complementary nucleotides may be present at a predetermined primer terminus as hereinbefore described.

It will be appreciated, however, that in certain circumstances synthesis of a diagnostic primer extension product might be induced to occur even in the presence of a non-complementary 3'-terminal residue. This artefactual result may arise from the use of too low a temperature in which case the temperature may be increased, too long a time of incubation/annealing in which case the time may be reduced, too high a salt concentration in which case the salt concentration may be reduced, too high an enzyme concentration, too high a nucleoside triphosphate concentration, an incorrect pH or an incorrect length of oligonucleotide primer. All of these factors are discussed in European Patent Publication No 237,362. A major source of artefactual products is probably allowing the reaction temperature to fall too low, thus permitting too low a stringency, for example by removing the reaction mixture from the heat cycling means, even briefly for example to add the agent for polymerisation (eg. Taq polymerase) especially in the first reaction cycle. In addition to the above we have found that such artefactual results may also arise from use of a diagnostic primer which is particularly rich in G (guanosine) and C (cytidine) residues. A diagnostic primer may give rise to difficulty in this regard if it is G/C rich as a whole or particularly if it is G/C rich at its relevant, normally, 3', end. Moreover the precise nature of the base pairing in the region of the relevant, normally 3', end of the diagnostic primer when in use may be the cause of an artefactual result. Thus the presence of As (adenosine) in the base pairing in the region of the relevant, normally 3', end of the diagnostic primer tends to improve specificity whilst the presence of Gs (guanosine) does not. Furthermore the precise nature of the mismatch at the relevant, normally 3', end of the diagnostic primer may be an important factor in whether or not an artefactual result is obtained. Thus for example an AA or CT mismatch does not normally result in hybridisation, but a GT or AC mismatch may result in a sufficient degree of hybridisation to result in the formation of artefactual product(s). Artefactual results may be avoided by deliberately introducing one or more further mismatched residues, or if desired, deletions or insertions, within the diagnostic primer to destabilise the primer by further reducing the binding during hybridisation.

Thus for example any one or more of the 10, for example 6 nucleotides adjacent to the terminal mismatch may be altered to introduce further mismatching. In general only one mismatch in addition to the terminal mismatch may be necessary, positioned for example, 1, 2 or 3 bases from the terminal mismatch. Thus, for example, in relation to the determination of the presence of a normal homozygote, heterozygote or affected homozygote in respect of the Z allele of the α1 antitrypsin gene we have found that good results may be obtained if the third nucleotide from the 3' terminal nucleotide is altered to generate a mismatch in use. Thus for example we have found that the presence of a C instead of an A as the third nucleotide from the 3' terminus of the diagnostic primer enables normal homozygotes, heterozygotes and affected homozygotes in respect of the Z allele to be readily distinguished. The best design of diagnostic primer may thus be determined by straightforward experimentation based on the above criteria, such experimentation being well within the ability of the skilled molecular biologist.

The term "diagnostic primer" is used herein to refer to the primer which has a nucleotide sequence such that a terminal nucleotide thereof is selected to be either complementary to the suspected variant nucleotide or to the corresponding normal nucleotide such that an extension product of the diagnostic primer is synthesised when the terminal nucleotide of the diagnostic primer is complementary to the appropriate terminal nucleotide of the corresponding diagnostic portion of the target base sequence, but no such extension product is synthesised when the terminal nucleotide of the diagnostic primer is not homologous with the appropriate terminal nucleotide of the corresponding diagnostic portion of the target base sequence.

The term "amplification primer" is used herein to refer to a primer which is capable of hydridising to the nucleic acid strand which is complementary to the nucleic acid strand to which the diagnostic primer is capable of hydridising, the "amplification primer" having a nucleotide sequence such that it is capable of hybridising to a diagnostic primer extension product, after separation from its complement, whereby the diagnostic primer extension product serves as a template for synthesis of an extension product of the amplification primer, thereby facilitating amplification.

The present invention is thus directed, at least in part, to an improvement of amplification processes, such as the process described in European Patent Publication No. 237, 362 in which the improvement renders it possible to selectively amplify either a sequence containing a suspected variant nucleotide if present or a sequence containing the corresponding normal nucleotide if present, thus simplifying detection whilst avoiding sequencing, allele specific oligonucleotides and restriction digestion. Thus for a given nucleotide variation, for example point mutation, its presence or absence may be detected either 1) by designing the diagnostic primer to have an appropriate terminal nucleotide which is complementary to the suspected nucleotide variation such that the synthesis of an amplified product will be indicative of the presence of the suspected nucleotide variation and the absence of an amplified product will be indicative of the absence of the suspected nucleotide variation; or 2) by designing the diagnostic primer to have an appropriate terminal nucleotide which is complementary to the corresponding normal nucleotide such that the synthesis of an amplified product will be indicative of the absence of the suspected nucleotide variation and the absence of an amplified product will be indicative of the presence of the suspected nucleotide variation. In this regard references herein to the "appropriate terminal nucleotide" means the terminal nucleotide of the primer from which in use synthesis would be initiated if possible. Thus since in general the agent for polymerisation would initiate synthesis at the 3' end of the primer, the appropriate terminal nucleotide would in general be the 3' terminal nucleotide.

Confirmation of the presence or absence of for example a given point mutation may be obtained by adopting both alternative procedure (1) and alternative procedure (2) as set out above. A combination of the two approaches provides a method for the detection of heterozygotes which will be of value for the analysis of dominant inherited conditions and in the detection of carriers of recessive inherited conditions.

In a preferred embodiment, the present invention is directed to detecting the presence or absence of more than one suspected variant nucleotide in the same sample. The ability of the present invention to selectively amplify sequences depending on the predetermined nucleotide sequence of the diagnostic primers enables multiple amplification products to be distinguished simply, accurately and with minimal operator skill thus making it possible to provide a robust technique for screening a single sample for multiple nucleotide variations. The present invention is thus of particular interest in screening a single sample of DNA or RNA for a battery of inherited conditions such as genetic disorders, predispositions and somatic mutations leading to various diseases. Such DNA or RNA may for example be extracted from blood or tissue material such as chorionic villi or amniotic cells by a variety of techniques such as those described by Maniatis et al, Molecular Cloning (1982), 280–281. Moreover as the molecular basis for further inherited conditions becomes known these further conditions may simply be included in the screening technique of the present invention.

Multiple amplification products may be distinguished by a variety of techniques. Thus for example probes may be employed for each suspected amplified product, each probe carrying a different and distinguishable signal or residue capable of producing a signal.

Such signals and residues capable of producing a signal are discussed in detail in our European Patent Publication No. 246,864, but might for example include the solid phase amplification system described by Wang, C. G. in World Biotech Report 1986 vol. 2, part 2 pages 33–37, (Diagnostics Healthcare Proceedings of the conference held in November 1986, San Francisco) in which microbeads formed with many chosen trace elements are conjugated to the probe. The presence of specific probes may be detected by x-ray fluorescent analysis. Such techniques would generally be simple and straightforward to apply since it would only be necessary to detect the existence of an amplification product rather than distinguish between sequences differing by as little as a single nucleotide.

A much simpler and preferred method of distinguishing between amplification products comprises selecting the nucleotide sequences of the amplification primers such that the length of each amplified product formed during the process of the present invention is different. In this regard the number of base pairs present in an amplification product is dictated by the distance apart of the diagnostic and amplification primers. Thus the amplification primers may be designed such that each potential variant nucleotide is associated with a potential amplification product of different length.

The presence or absence of a given potential variant nucleotide may thus advantageously be detected by electrophoretic techniques, in which the different amplified products obtained may be distributed according to their molecular weight and thereby identified for example by autoradiography or fluorescent techniques. The lengths of the different products may only differ by a single nucleotide, but preferably the lengths will differ by at least 3 nucleotides. The process of the present invention is preferably effected by the use of an intercalating dye such as ethidium bromide which may be visualised as an orange fluorescence upon ultraviolet irradiation. Thus the presence or absence of a plurality of potential variant nucleotides in a single sample may be rapidly, accurately and easily determined. If desired the diagnostic primer(s) and/or the amplification primer(s) may be marked or labelled for example by the use of a fluorophore. Thus, for example, each different diagnostic primer or amplification primer may carry a different fluorophore so that the results of a battery of tests may be read from an electrophoresis gel for example by a laser scanner, thus enabling automation of the method of the present invention. Alternatively the presence or absence of an amplified product may simply be assessed by the use of a solvent capable of selectively dissolving nucleoside triphosphates, but not capable of dissolving a nucleotide sequence (for example DNA). Trichloroacetic acid (TCA) is an example of such a solvent. Thus for example the presence or absence of an amplified product may be determined by TCA precipitation of amplified reaction mixtures. Where incorporation of the appropriate nucleoside triphosphates has occurred in an exponential reaction series then substantially greater amounts of TCA insoluble material will be present than where no extension of the diagnostic primer has occurred. Quantification of insoluble material might be accomplished by known methods. Thus for example the nucleoside triphosphates might be labelled (for example by a radioactive or fluorescent marker), the reaction mixture may be subjected to for example centrifugation, the liquid present decanted off and either the liquid or the insoluble product subjected to appropriate detection techniques such as radioactive counting or fluorescence determination.

According to a further feature of the present invention we provide a nucleotide sequence of from about 5 to 50 bp for use in the method of the present invention, a terminal nucleotide of said sequence being complementary to either a suspected variant nucleotide associated with a known genetic disorder or to the corresponding normal nucleotide, the remainder of the said sequence being substantially complementary to the corresponding target base sequence adjacent the suspected variant nucleotide or corresponding normal nucleotide, the said nucleotide sequence being such that when used as a diagnostic primer in the method of the present invention an extension product of the diagnostic primer is synthesised when the said terminal nucleotide of the diagnostic primer is complementary to the corresponding nucleotide in the target base sequence, no extension product being synthesised when the said terminal nucleotide of the diagnostic primer is not complementary to the corresponding nucleotide in the target base sequence.

Conveniently the terminal nucleotide being complementary to either a suspected variant nucleotide or to the corresponding normal nucleotide is at the 3' end of the nucleotide sequence. Preferably the suspected variant nucleotide results from a point mutation of the corresponding normal sequence.

The said nucleotide sequence may for example be of 10 to 50 bps, for example 10 to 36 bps.

According to four further features of the present invention we provide nucleotide sequences as defined immediately above and wherein a terminal nucleotide of the nucleotide sequence is complementary to a variant nucleotide resulting from a change of the corresponding normal nucleotide to (i) A, (ii) G, (iii) C, (iv) T or U respectively.

According to a further feature of the present invention we provide a set of two nucleotide sequences as defined above, a terminal nucleotide of one sequence being complementary to a suspected variant nucleotide associated with a known genetic disorder and a terminal nucleotide of the other sequence being complementary to the corresponding normal nucleotide.

According to a still further feature of the present invention there are provided probes comprising a nucleotide sequence as hereinbefore defined carrying a label or marker component.

By way of example the following known genetic disorders are detailed showing the mutations responsible for the disorder and a relevant literature reference for each mutation. Nucleotide sequences and probes as hereinbefore defined may for example be based on the genetic disorders detailed below, the sequence of the relevant nucleotide sequence or probe being derivable from the relevant literature reference specified in the Table.

TABLE

Mutations causing genetic disease

A Autosomal

| Disease | Mutation | Reference |
| --- | --- | --- |
| Antithrombin III deficiency | CG → TG | Duchange et al Nucleic Acids Research 14:2408 (1986) |
| Amyloidotic polyneuropathy | CG → CA | Maeda S. et al., Mol. Biol. Med, 329–338 (1986) |
| | AC → GC | Wallace M R. et al, J. Clin Invest 78:6–12 (1986) |
| | AG → GG | Wallace M R. et al, J. Clin. Invest 78:6–12 (1986) |
| Alpha-1-antitrypsin deficiency | TG → CG | Nukiwa T. et al., J. Biol. Chem. 261:15989–15994 (1986) |
| | CG → CA | Kidd V J et al., Nature 304:230–234 (1983) |
| | GAT → GTT | Asp 256 - Val, Exon III; unreported. |
| | CTT → CTC | deletion of codon 51 (normal) M Malton, in press. |
| | GGC → TGC | Arg$^{39}$ - Cys, Exon II; I variant, unreported. |

| Base-pair | Mutation | Reference |
| --- | --- | --- |
| Adenosine deaminase deficiency | CG → CA | Bonthron D T. et al., J. Clin Invest 76:894–897 (1985) |
| | AA → AG | Valerio D. et al EMBO J 5:113–119 (1986) |
| | CT → CG | Valerio D. et al EMBO J 5:113–119 (1986) |
| Apolipoprotein E deficiency | GT → GC | Cladaras et al J. Biol. Chem 262:2310–2315 (1987) |
| Diabetes mellitus, mild | TC → CC | Haneda M. et al., Proc. Natl. Acad. Sci. USA 80:6366–6370 (1983) |
| | TC → TG | Shoelson S. et al., Nature 302:540–543 (1983) |
| | TG → TT | Shoelson S. et al., Nature 302:540–543 (1983) |
| Gaucher's disease type 2 | CT → CC | Tsuji S. et al., N. Engl. J. Med. 316:570–575 (1987) |
| Hyper-insulinaemia, familial | CG → CA | Shibasaki Y. et al., J. Clin. Invest 76:378–380 (1985) |
| | CA → GA | Chan S J. et al., Proc. Natl. Acad. Sci USA 84:2194–2197 (1987) |

| Disease | Mutation | Reference |
| --- | --- | --- |
| Immunoglobulin kappa deficiency | CT → CG | Stavnezer-Nordgren J. et al., Science 230: 458–461 (1985) |
| | CG → TG | Stavnezer-Nordgren J. et al., Science 230: 458–461 (1985) |
| LDL receptor deficiency | GG → GA | Lehrman M A et al., Cell 41:735–743 (1985) |
| Osteogenesis imperfecta (type II) | TG → TT | Cohn D H et al., Proc Natl Acad Sci USA 83:6045–6047 (1986) |
| Phenylketonuria | AG → AA | Dilella A G et al Nature 322:799–803 (1986) |
| | CG → TG | Dilella A G et al., Nature 327:333–336 (1987) |
| Protein C deficiency | CG → TG | Romeo G. et al Proc Natl Acad Sci USA 84:2829–2832 (1987) |
| | GG → GC | Romeo G. et al Proc Natl Acad Sci USA 84:2829–2832 (1987) |
| Purine nucleoside phosphorylase deficiency | TG → TA | Williams S R. et al., J. Biol. Chem. 262: 2332–2339 (1987) |
| Sickle cell anaemia | GAG → GTG | Chang J C. and Kan Y W. Lancet 2, 1127–9 (1981); Orkin S H. et al., New Eng. |

TABLE-continued

| | | | |
|---|---|---|---|
| Tangier disease | AG → AT | | J. Med. 307, 32–6 (1982); and Conner B J et al Proc. Natl. Acad. Sci. USA., 80, 278–82 (1983). Law S W. Brewer H B J. Biol. Chem 260:12810–128814 (1985) |

Disease
β-Thalassaemia

| Mutant Class | Type | Reference | |
|---|---|---|---|
| a) non-functional mRNA Nonsense mutants | | | |
| (1) codon 17 (A → T) | O | Chang J C et al Proc. Natl. Acad. Sci. USA 76:2886 (1979) | |
| (2) codon 39 (C → T) | O | Trecartin R F et al J. Clin. Invest. 68: 1012 (1981) and Chehab, F F et al Lancet i:3 (1986) | |
| (3) codon 15 (C → A) | O | Kazazian H H et al Eur. Molec. Biol. org. J. 3:593 (1984) | |
| (4) codon 37 (G → A) | O | Boehm. C D et al Blood 67:1185 (1986) | |
| (5) codon 121 (G → T) | O | Kazazian H H et al. Am. J. Hum. Genet. 38:A860 (1986) | |
| Frameshift mutants | | | |
| (6) − 2 codon 8 | O | Orkin S H et al., J. Biol. Chem. 256: 9782 (1981) | |
| (7) − 1 codon 16 | O | Kazazian H H et al Eur. molec. biol. org. J. 3:593 (1984) | |
| (8) − 1 codon 44 | O | Kinniburgh. A J et al Nucleic Acids Res 10:5421 (1982) | |
| (9) − 1 codons 8/9 | O | Kazazian H H et al Eur. molec. biol. org. J. 3:593 (1984) and Wong C et al Proc. Natl. Acad. Sci. USA 83:6529 (1986) | |
| (10) − 4 codons 41/42 | O | Kazazian, H H et al Eur. molec. biol. org. J 3:593 (1984) and Kimura, A et al J. Biol. Chem. 258: 2748 (1983) | |
| (11) − 1 codon 6 | O | Kazazian H H et al Am. J. Hum. Genet. 35: 1028 (1983) | |
| (12) + 1 codons 71/72 | O | Cheng T C et al Proc. Natl. Acad. Sci. USA 81:2821 (1984) | |
| (b) RNA processing mutants Splice junction changes | | | |
| (1) IVS 1 position 1 GT → AT | O | Orkin, S H et al Nature 296:627 (1982) and Treisman R, et al Nature 302:591 (1983) | |
| (2) IVS 1 position 1 GT → TT | O | Kazazian, H H et al Eur. molec. biol. org. J. 3:593 (1984) | |
| (3) IVS 2 position 1 GT → AT | O | Orkin, S H et al, Nature 296, 627 (1982) and Treisman, R et al Cell 29:903 (1982) | |
| (4) IVS 1 3' end: −17 bp | O | Bunn H F et al, Haemoglobin: molecular genetic and clinical aspects, p. 283 (Saunders, Philadelphia 1986) Kazazian, H H et al., Eur. molec. Biol. org. J., 3: 593 (1984) and Orkin, SH et al. J. Biol. Chem. 258: 7249 (1983). | |
| (5) IVS 1 3' end: −25 bp | O | | |
| (6) IVS 2 3' end: AG → CG | O | Padanilam B J, et al Am. J. Hematol 22:259 (1986) | |
| (7) IVS 2 3' end: AG → CG | O | Antonarakis S E, et al Proc. Natl. Acad. Sci. USA 81:1154 (1984) and Atweh G F et al Nucleic Acids Res. 13: 777 (1985). | |
| Consensus changes | | | |
| (8) IVS 1 position 5 (G → C) | + | Kazazian, H H et al Eur. molec. Biol. org. J. 3:593 (1984) and Treisman, R et al Nature 302:591 (1983) | |
| (9) IVS 1 position (G → T) | O | Wong C et al Proc. Natl. Acad. Sci. USA 83:6529 (1986) and Atweh, G F et al Nucleic Acids Res. 13: 777 (1985). | |
| (10) IVS 1 position 6 (T → C) | + | Orkin, S H et al Nature 296:627 (1982) and Atweh G F et al Am. J. Hum. Genet 38:85 (1986) | |
| Internal IVS changes | | | |
| (11) IVS 1 position 110 (G → A) | + | Westaway, D et al Nucleic Acids Res. 9: 1777 (1981) | |
| (12) IVS 2 position 705 (T → G) | + | Dobkin, C et al Proc. Natl. Acad. Sci. USA 80:1184 (1983). | |
| (13) IVS 2 position 745 (C → G) | + | Orkin, S H et al Nature 296:627 (1982) and Treisman, R et al Nature 302:591 (1983) | |
| (14) IVS 2 position 654 (C → T) | O | Cheng T C et al Proc. Natl. Acad. Sci. USA 81:2821 (1984) | |
| (15) IVS 1 position 116 (T → G) | ? | Feingold E A et al Ann. N. Y. Acad. Sci 445:159 (1985) | |
| Coding region substitutions | | | |
| (16) codon 26 (G → A) | β+, βε | Thein S L et al J. Med. Genet. (in press 1986) and Orkin S H et al Nature 300:768 (1982) | |
| (17) codon 24 (T → A) | + | Goldsmith et al Proc. Natl. Acad. Sci USA 88:2318 (1983) | |
| (18) codon 27 (G → T) | β+, βK nos sos | Orkin S H et al Blood 64:311 (1984) | |
| (c) Transcriptional mutants | | | |
| (1) −88 C → T | + | Wong, C et al Proc. Natl. Acad. Sci. USA 83:6529 (1986) Orkin S H et al J. Biol. Chem. 259: 8679 (1984) | |
| (2) −87 C → G | + | Orkin S H et al Nature 296:627 (1982) and Treisman R et al Nature 302:591 (1983) | |
| (3) −31 A → G | + | Takihara Y et al Blood 67:547 (1986) | |

TABLE-continued

| | | | |
|---|---|---|---|
| (4) −29 A → G | + | | Antonarakis S E et al<br>Proc. Natl. Acad. Sci. USA<br>81:1154 (1984)<br>and Wong C et al<br>Proc. Nat. Acad. Sci. USA<br>83:6529 (1986) |
| (5) −28 A → C | + | | Surrey S et al<br>J. Biol. Chem. 260:6507<br>(1985) |
| (6) −28 A → G | + | | Orkin S H et al<br>Nucleic Acids Res.<br>11:4727 (1983) |
| (d) Polyadenylation mutant | | | |
| (1) AATAAA →<br>AACAAA | + | | Orkin S H et al<br>Eur. molec. Biol. org. J.<br>4:453 (1985) |
| (e) Deletions | | | |
| (1) 3'β(−619bp) | O | | Spritz. R A et al<br>Nucleic Acids Res.<br>10:8025 (1982)<br>and Orkin, S H et al<br>Proc. Natl. Acad. Sci. USA<br>76:2400 (1979) |
| (2) 5'β(−1.35kb) | O HbF | | Padanilam. B J et al<br>Blood 64:941 (1984) |
| (3) β (−10kb) | O HbF | | Gilman. J G et al<br>Br. J. Haemat. 56:339<br>(1984) |

+ = β-Thalassaemia mutant (β⁻) which causes reduced β-globin chain production: 0 = a mutant (B°) which causes absent β-globin chain production.

| Disease | Mutation | Reference |
|---|---|---|
| Triosephosphate isomerase deficiency | AG → AC | Daar I O. et al., Proc. Natl. Acad. Sci USA 83:7903–7907 (1986) |
| Uroporphyrinogen decarboxylase deficiency B X-linked | GG → GA | De Verneuil H. et al., Science 234:732–734 (1986) |

| Disease | Gene | Mutation | Reference |
|---|---|---|---|
| Haemophilia A | Factor VIII | CG → TG (24) | Gitschier J. et al., Nature 315:427–430 (1985) |
| | | CG → TG (26) | Gitschier J. et al., Nature 315:427–430 (1985) |
| | | CG → TG (18) | Antonarakis S E et al., N. Engl. J. Med. 313:842–848 (1985) |
| | | CG → CA (26) | Gitschier J. et al., Science 232:1415–1416 (1986) |
| | | CG → TG (18) | Youssoufian H. et al., Nature 324:380–382 (1986) |
| | | CG → TG (22) | Youssoufian H. et al., Nature 324:380–382 (1986) |
| | | CG → TG (22) | Youssoufian H. et al., Nature 324:380–382 (1986) |
| Haemophilia B | Factor IX | CG → CA | Bentley A K et al., Cell 45:343–348 (1986) |
| | | GT → TT | Rees D J G et al., Nature 316:643–645 (1985) |
| | | GA → GG | Davis L M et al., Blood 69:140–143 (1987) |

Examples of deletions are to be found in:

Forrest, S. M., Cross, G. C., Speer, A., Gardner-Medwin, D., Burn, J., and Davies, K. E. (1987) Preferential deletion of exons in Duchenne and Becker muscular dystrophies. Nature 320, 638–640.

Koenig, M., Hoffman, E. P., Bertselson, C. J., Monaco, A. P., Feener, C. and Kunkel, L. M. (1987) Complete cloning of the Duchenne muscular dystrophy (DMD) cDNA and preliminary genomic organisation of the DMD gene in normal and affected individuals. Cell 50, 509–517.

Malhotra, S. B., Hart, K. A., Klamut, H. J., Thomas, N. S. T., Bodrug, S. E., Burghes, A. H. M., Bobrow, M., Harper, P. S., Thompson, M. W., Ray, P. N. and Worton, R. G. (1988) Frame-shift deletions in patients with Duchenne and Becker muscular dystrophy, Science 242, 755–759.

Read, A. P., Mountford, R. C., Forrest, S. M., Kenwrick, S. J., Davies, K. E. and Harris, R. (1988) Patterns of exon deletions in Duchenne and Becker muscular dystrophy. Hum. Genet. 80, 152–156.

Chamberlain, J. S., Gibbs, R. A., Ranier, J. E., Nguyen, P. N. and Caskey, C. T. (1988) Deletion screening of the DMD locus via multiplex DNA amplification. Nuc. Ac. Res. 16; 23, 11141–11156.

Roberts, R. G., Cole, C. G., Hart, K. A., Bobrow, M. and Bentley, D. R. (1989) Rapid carrier and prenatal diagnosis of Duchenne and Becker muscular dystrophy, Nuc. Ac. Res. 17; 2,811.

Often only small quantities of genomic DNA are available for analysis. It has been found that the specificity of diagnostic primers for relevant normal or variant nucleotide sequences can be conveniently assessed by increasing the number of copies of the nucleotide sequence(s) in the hybridisation assay. This may for example be achieved by constructing a double stranded "cassette" comprising a normal sequence annealed to a variant sequence the mismatch between two nucleotides on adjacent strands preferably being present towards the middle of the cassette. Copies of the cassette are then conveniently obtained by its insertion into a plasmid host followed by replication of the plasmid and isolation of the desired sequences, all using techniques well known in the art. This technique is conveniently illustrated in FIG. 10.

In order that the present invention may be more fully understood it is described hereinafter, by way of example, with reference to the accompanying drawings, in which:

FIGS. 1(a) and 1(b) illustrate the first embodiment of the invention, FIG. 1 (c) illustrating a typical result of such a test as might be shown electrophoretically;

FIGS. 2(a) and 2(b) illustrate the second embodiment of the present invention;

FIG. 3 illustrates a preferred method for distinguishing between multiple amplification products;

FIGS. 4(a) and 4(b) illustrate the third embodiment of the present invention;

FIGS. 5(a), (b) and (c) illustrate the fourth embodiment of the present invention;

Figure 11A:
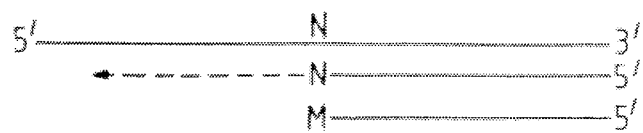
Figure 11B:
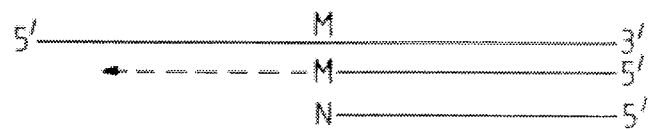
Figure 11C:
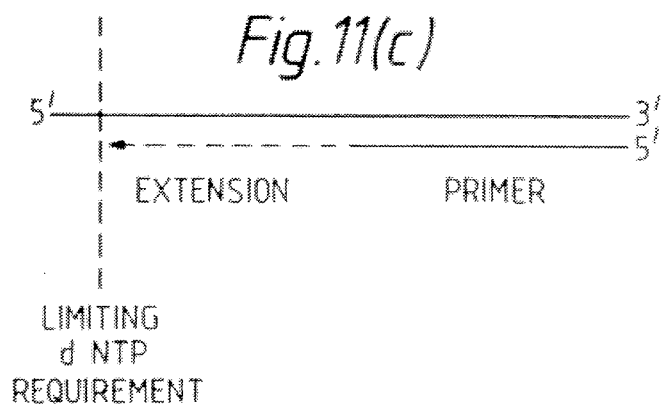

FIGS. 11A–C illustrate the fifth embodiment (linear amplification) of the invention.

Figure 12:
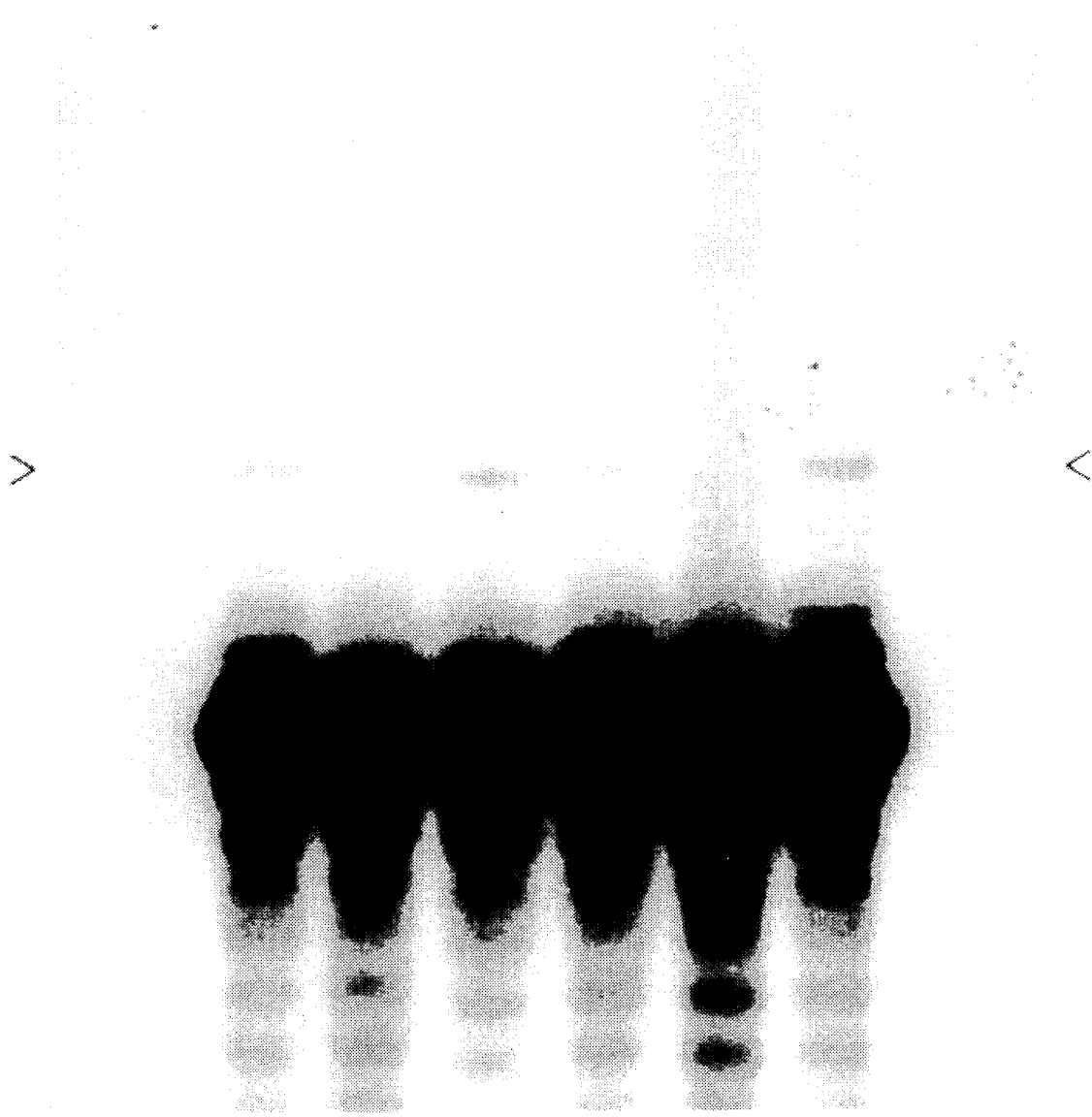

FIG. 12 shows the results of visualisation of the gel obtained in Example 5.

Figure 13:
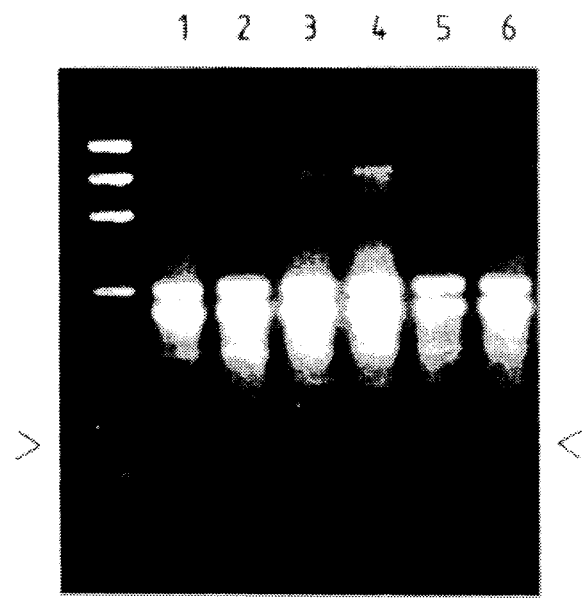

FIG. 13 shows the results of visualisation of the gel obtained in Example 6.

Figure 1A:
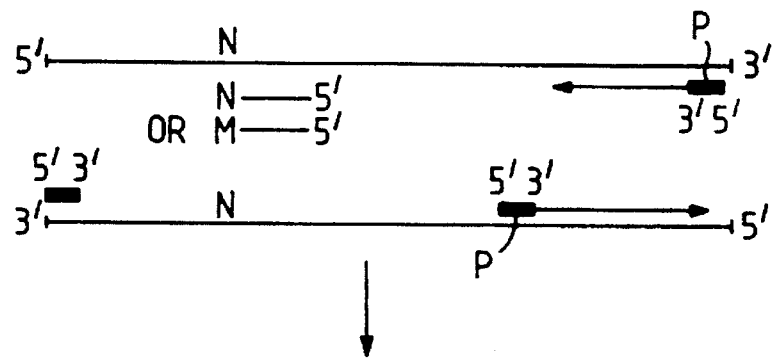
Figure 1B:
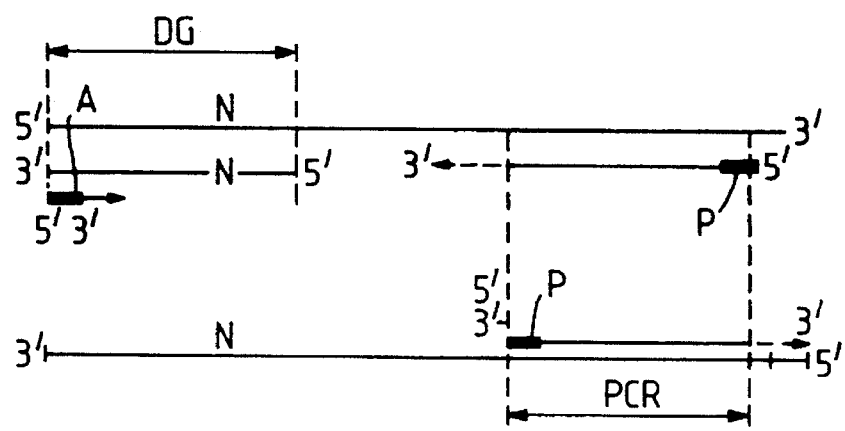
Figure 1C:
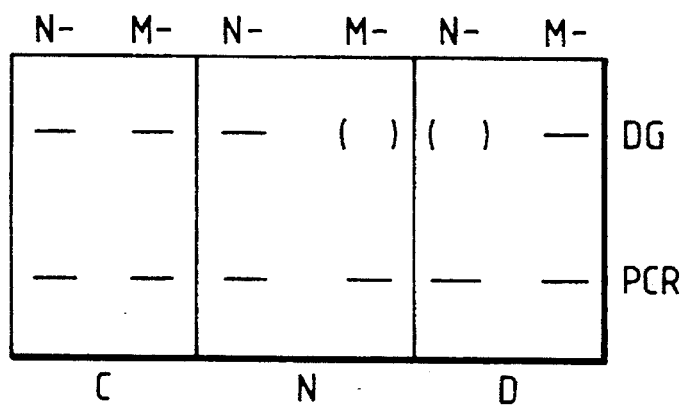

FIG. 1 illustrates the method of the first embodiment of the present invention. FIG. 1(a) shows denatured genomic DNA strands containing a normal nucleotide (N) in the position in which, for example as a result of a genetic disorder, a suspected variant nucleotide might be present. Contacting the nucleic acid strand, under hybridising conditions, with a diagnostic probe having a 3'-terminal nucleotide complementary to the normal nucleotide (-N) in the presence of appropriate nucleoside triphosphates and an agent for polymerisation of the nucleoside triphosphates results in chain extension of the diagnostic primer in the 3'-direction as shown in FIG. 1(b). No such chain extension arises where a diagnostic primer is used in which the 3'-terminal nucleotide is complementary to the suspected variant nucleotide (-M). Any chain extension product of the diagnostic primer may then be denatured and an amplification primer (A) hybridised to the denatured product obtained to yield a further chain extension product. The chain extension product may then be denatured and the process repeated to achieve amplification. The region of the genomic DNA subject to amplification with the diagnostic primer is designated DG in FIG. 1(b). The diagnostic products from this region are responsible for the bands designated DG in FIG. 1(c). As a control, PCR (polymerase chain reaction) primers (P) designated P in FIG. 1(a) may be employed at a separate site on the nucleic acid strand or on another nucleic acid strand, for example on another chromosome in consideration for example of human DNA. This separate site is designated PCR in FIG. 1(c) and the PCR control products from this site are responsible for the bands designated PCR in FIG. 1(c). It will be appreciated that the bands designated PCR may represent either larger or smaller products than the product represented by the band designated DG.

FIG. 1(c) shows the result of the method shown in FIG. 1(a) and 1(b), in the form of bands resolved on agarose gel electrophoresis in relation to for example a genetic disorder caused by a point mutation analysed using either the -M or -N diagnostic primer as appropriate. Where the subject tested is a carrier (C) of the genetic disorder bands will be seen in respect of both the normal (N) nucleotide sequences and the variant nucleotide sequence (M). Normal homozygotes (N) will show a band present in respect of the normal nucleotide sequence, but no band [depicted as ()] present in respect of the variant nucleotide and homozygotes for the disease causing mutation (subjects with the genetic disorder (D) will show no band [depicted as ()] present in respect of the normal nucleotide sequence and a band present in respect of the variant nucleotide sequence.

Figure 2A:
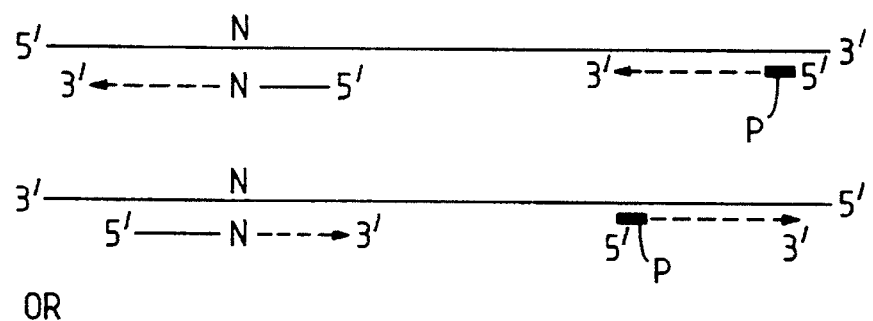
Figure 2B:
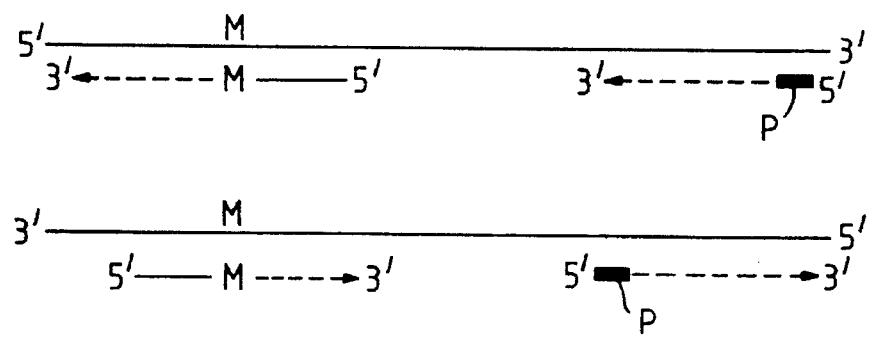

FIG. 2 illustrates the second embodiment of the present invention. A diagnostic primer is employed for each strand of a double stranded nucleic acid. In (a) the diagnostic primers are designed such that the 3'-terminal nucleotide is complementary to the normal nucleotide. The method thus proceeds as described in relation to FIG. 1, but with two different diagnostic primers initiating amplification if the relevant nucleotide is present. Thus in this embodiment the second diagnostic primer is equivalent to the amplification primer (A) in FIG. 1. Thus in FIG. 2(a) amplification will be initiated by the primers (-N and N-) but not by diagnostic primers having 3'-terminal nucleotides complementary to the variant nucleotide sequence (-M and M-). The reverse is true in FIG. 2(b) since the variant sequence is present in the nucleic acid strands of the sample. The results of effecting the method shown in FIG. 2 may be represented in a manner similar to that shown in FIG. 1(c), but the references therein to normal and variant (N and M) will correspond to pairs of such sequences. In FIG. 2 the letter P refers to the PCR primers used as a control.

Figure 3:
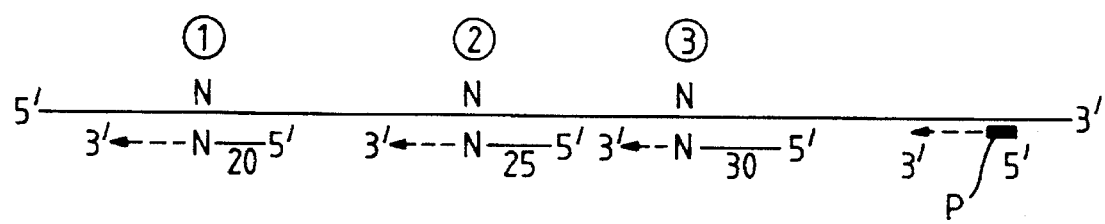
Figure 3:
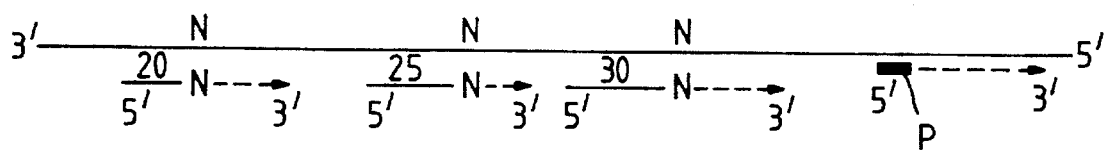

FIG. 3 shows one way in which multiple amplification products may be distinguished thus enabling a single sample of RNA or DNA to be tested for a battery of inherited conditions. Two strands (denatured) of DNA or RNA of a sample are depicted as containing three separate loci numbered 1, 2 and 3. A further region removed from these loci is used for PCR amplification to serve as a control. In respect of locus (1) a 20-met diagnostic primer (5'-N 3') is used together with a further 20 mer (3'N- 5') diagnostic primer. If amplification takes place at locus (1) a 39-mer amplification product will be obtained. Since in the Figure the 3'-terminal nucleotide is normal as is the relevant nucleotide in the test sample, amplification will take place. Similarly amplification will take place if the relevant nucleotide in the test sample is a variant nucleotide and the diagnostic primers used also carry a 3'-terminal variant nucleotide.

No such amplification will however arise where a mismatch arises between the relevant nucleotide in the sample and the 3'-terminal nucleotide of the diagnostic primer. At locus (2) the diagnostic primers are designed to yield a 49-mer amplification product if amplification takes place and at locus (3) the diagnostic primers are designed to yield a 59-mer amplification product if amplification takes place. Since as may be seen from the above, amplification product band size is the sum of the sizes of the two diagnostic primers minus one, it is possible to conduct multiple tests on a single sample in a single reaction vessel by appropriately designing the individual diagnostic primers to characterise each locus of interest. As the size of the sum of the sizes of the diagnostic primers increases, so amplification products can be resolved for example on agarose gels. Improved resolution may be possible if the diagnostic primers are labelled or marked in any convenient manner and then resolved for example on an acrylamide gel. In FIG. 3 the letter P refers to the PCR primers used as a control.

Figure 4A:
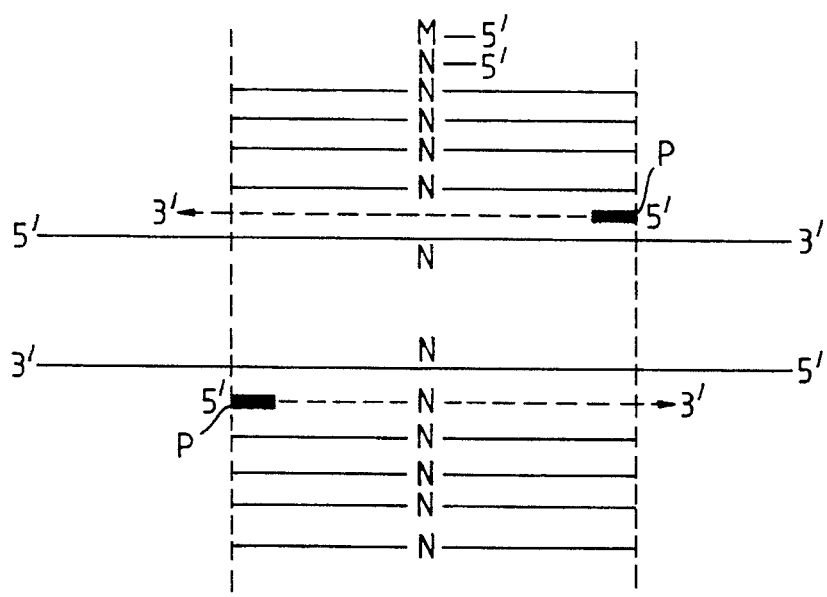
Figure 4B:
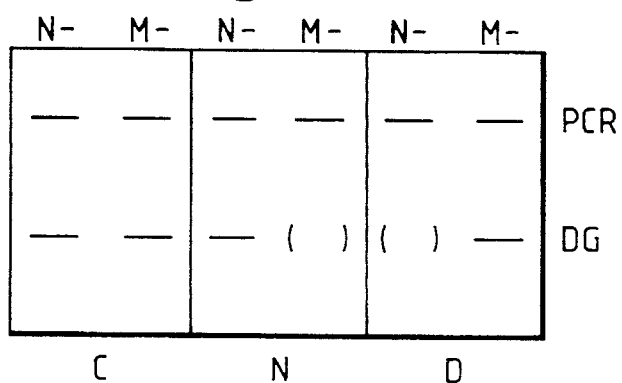

FIG. 4 shows the third embodiment of the present invention in which conventional amplification is effected of a nucleic acid sequence containing a normal nucleotide in the position in which a suspected variant nucleotide might be present, for example conventional PCR primers being used. Similarly conventional amplification would take place if the suspected variant nucleotide were present instead of the normal nucleotide. The amplification product is contacted with a diagnostic primer as described hereinbefore in relation to the third embodiment of the invention. Where the amplified product comprises a nucleic acid sequence containing a normal nucleotide as described above and the diagnostic primer is used having a 3'-terminal normal nucleotide, an extension product of diagnostic primer will be formed [using the nucleotide sequence produced by conventional PCR amplification, (referred to herein as the PCR control product) as a template] provided appropriate nucleoside triphosphates and an agent for polymerisation of the nucleoside triphosphates are present. No amplification primer will be necessary since the template for production of the diagnostic primer extension product will already have been amplified. The presence or absence of the diagnostic primer extension product designated DG in FIG. 4(b)) as well as the presence of the PCR control product (designated PCR in FIG. 4(b) may be detected, for example by electrophoretic techniques.

It will be appreciated that a diagnostic primer extension product will also be formed where the PCR control product contains a variant nucleotide and the diagnostic primer employed has a 3'-terminal complementary variant nucleotide.

The resulting product bands may be visualized for example as shown in FIG. 4(b). The symbols N-, M-, C-, N, D, DG and PCR are as defined in relation to FIG. 1(c). The diagnostic primer extension product band however has a lower molecular weight than the PCR control band (as shown in FIG. 4b). In this case the control band represents a true internal control since one of the PCR primers serves as the amplification primer for amplification of the diagnostic primer extension product. Where the PCR control product contains a variant nucleotide and the diagnostic primer has a 3'-terminal normal nucleotide and vice versa no extension product will be formed.

If desired the third embodiment of the present invention may be effected by contacting the sample to be tested at the start of the test with not only the PCR primers, but also with the diagnostic primer. It is thus not necessary to delay use of the diagnostic primer until a desired degree of amplification of the PCR control product has been achieved. Indeed the diagnostic primer may be used together with or at any time after the PCR primers have been employed. The test may therefore be effected, for example, by simple addition of the sample to be tested to a single container, which container includes the PCR primers, the diagnostic primer, appropriate nucleoside triphosphates and an agent for the polymerisation of the nucleoside triphosphates. The products obtained and thus the product bands seen will be the same as described above and depicted in FIG. 4.

Figure 5A:
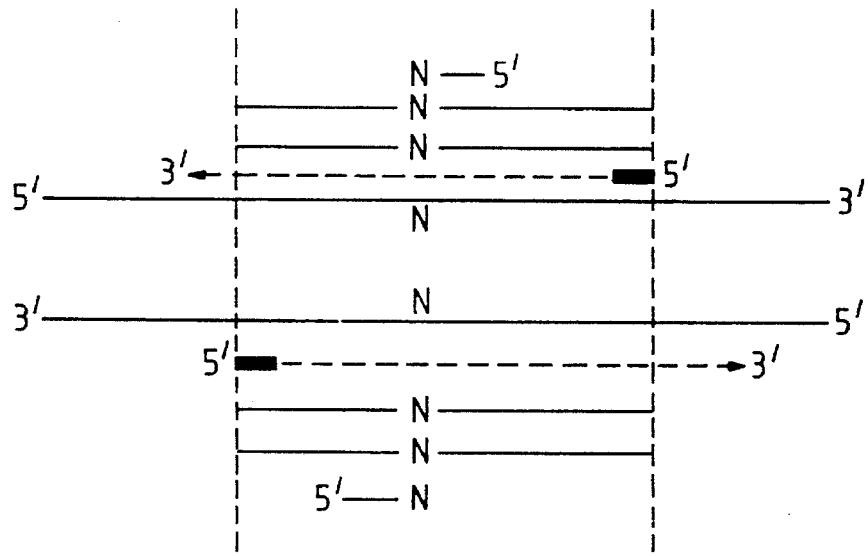
Figure 5B:
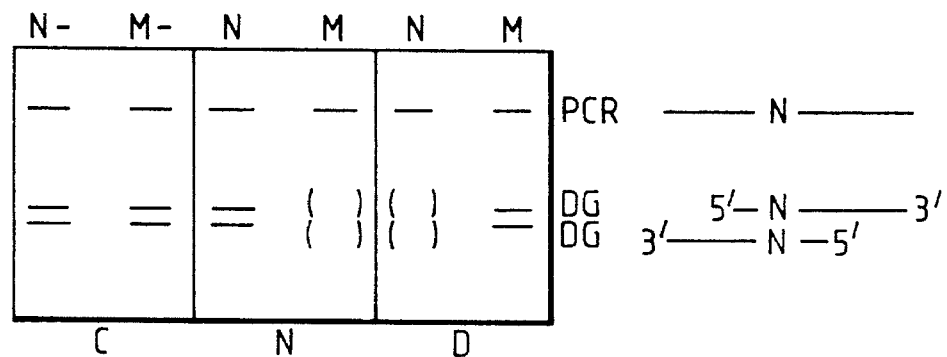
Figure 5C:
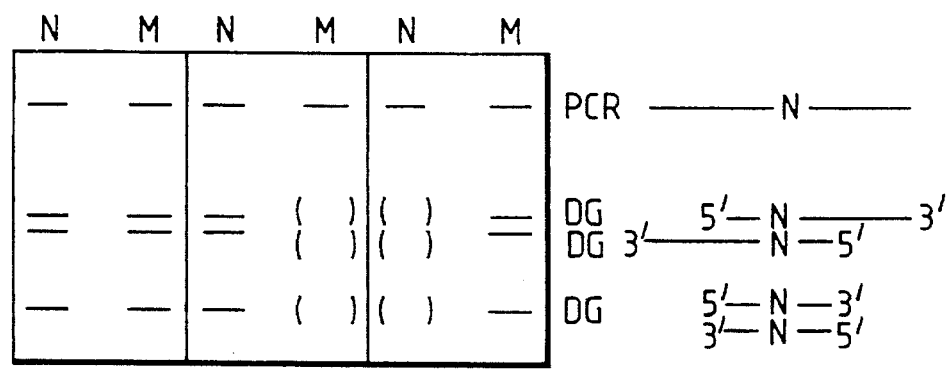

FIG. 5 depicts the fourth embodiment of the present invention in which conventional amplification is effected as described in relation to FIG. 4. The amplification product thus obtained is then contacted under hybridisation conditions with either (a) two separate diagnostic primers as hereinbefore defined each having a 3'-terminal normal nucleotide or b) two diagnostic primers as hereinbefore defined, each having a 3'-terminal variant nucleotide (see FIG. 5a). The formation of extension products following a single cycle will demonstrate whether the sample nucleic acid contains the normal or suspected variant nucleotide, electrophoretic techniques yielding a band pattern similar to that shown in FIG. 5b. It will be appreciated however that where two diagnostic primers are used, one diagnostic primer serves as the amplification primer for the other diagnostic primer. If desired therefore any extension product(s) obtained may themselves be subjected to amplification. Thus after multiple further cycles lower molecular weight products such as those shown by the additional band in FIG. 5c will be formed in ratios depending on the relative ratios of the original PCR primer oligonucleotides and the added diagnostic primers. The PCR amplification products may readily be distinguished from the diagnostic primer extension amplification products by for example increasing or decreasing the distance apart of the binding sites of the PCR primers on the genome.

If desired the fourth embodiment of the present invention may be effected by contacting the sample to be tested at the start of the test with not only the PCR primers, but also with the diagnostic primers. It is thus not necessary to delay use of the diagnostic primer until a desired degree of amplification of the PCR control product has been achieved. Indeed the diagnostic primers may be used together with or at any time after the PCR primers have been employed. The test may therefore, be effected for example, by simple addition of the sample to be tested to a single container, which container contains the PCR primers, the diagnostic primers, appropriate nucleoside triphosphates and an agent for the polymerisation of the nucleoside triphosphates. If the test is performed in this way the lower molecular weight diagnostic products referred to above will be formed thus giving rise to the additional bands depicted in FIG. 5.

Figure 6:
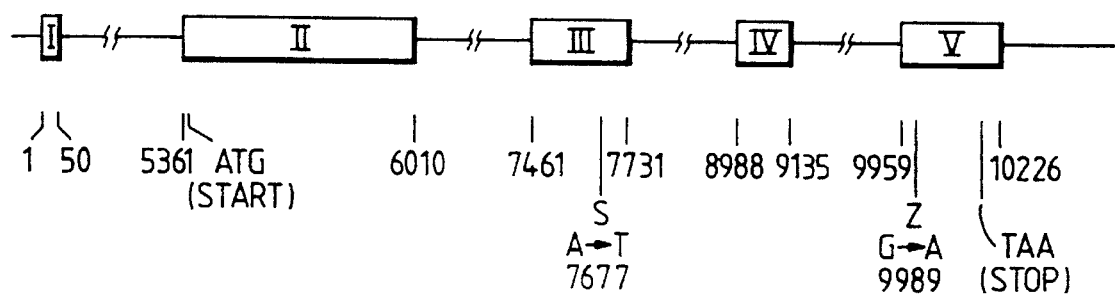
FIG. 6 (not to scale) depicts the human α1 antitrypsin gene.

FIG. 6 (not to scale) depicts the human α1 antitrypsin gene which is well known in the art [Long, G. L., et al Biochemistry Vol 23 p4828–4837, (1984)] shows inter alia the relative positions of the exons III and V which respectively carry the potential S and Z mutations of the α1 antitrypsin protein. In particular the figure depicts exon III of the α1 antitrypsin gene and shows the position of the S variant in which the codon GAA is mutated to GTA resulting in production of a valine residue at amino acid 264 in place of a glutamic acid residue. A primer I having the sequence.

5' CCCACCTTCCCCTCTCTCCAGGCAAATGGG 3'     I which hybridises to positions 7440–7469 of the α1 antitrypsin gene, and either a primer II having the sequence:

5' GGGCCTCAGTCCCAACATGGCTAAGAGGTG 3'     II or a primer IIa (a CT 3' mismatch based on II) having the sequence:

5' GGGCCTCAGTCCCAACATGGCTAAGAGGTT 3'     IIa each of which is designed for positions 7770–7799 of the α1 antitrypsin gene, can be conveniently used.

The Figure further depicts exon V of the α1 antitrypsin gene and shows the position of the Z variant in which the codon GAG is mutated to AAG resulting in the production of a lysine residue at amino acid position 342 in place of a glutamic acid residue. A primer III having the sequence:

5' TGTCCACGTGAGCCTTGCTCGAGGCCTGGG 3'     III which hybridises to positions 9890–9919 of the α1 antitrypsin gene, and a primer IV having the sequence:

5' GAGACTTGGTATTTTGTTCAATCATTAAG 3'     IV which hybridises to positions 10081–10109 of the α1 antitrypsin gene, can be conveniently used. The base numbering detailed above is in accordance with Biochem, 23 4828–4837, 1984.

Figure 7:
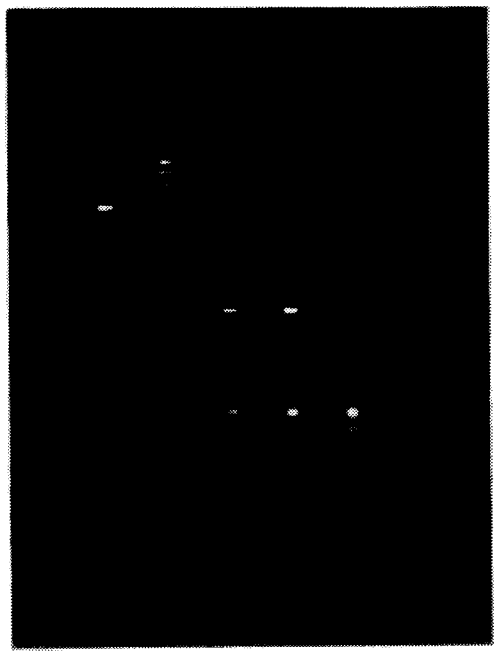
FIG. 7 shows the result of visualisation of the gel obtained in Examples 1 and 2.

FIG. 7 shows the result of visualisation of the gel obtained in Examples 1 and 2. Lane 1 represents a plasmid containing Exon V and cleaved with Alu I; Lane 2 shows a size marker being the bacteriophage φ X174 DNA cleaved with Hae III; Lane 3 shows amplification of Exon III with primers I and II as hereinbefore defined and amplification of Exon V with primers III and IV as hereinbefore defined in the same reaction mixture to yield products of 360 bp and 220 bp respectively. Lane 4 shows that no amplification of Exon III has taken place using primers I and IIa as hereinbefore defined, but that amplification of Exon V with primers III and IV as hereinbefore defined has been effected. Lane 5 shows a negative control in which primers I, II, III and IV are present under conditions effective to promote amplification, but in which no genomic DNA is present.

Figure 8:
FIG. 8 shows the result of visualisation of a gel in which Lanes 1–4 represent the results of Example 3, Lanes 5–8 represent a proportion of the results of Example 4 and Lane 9 represents a size marker.

FIG. 8 shows in Lanes 1–3 the results of Example 3, in Lanes 5–8 the results of using normal and mutant diagnostic primers in which no destabilisation has been effected in accordance with Example 4 and Lane 9 shows the size marker bacteriophage φ X174. Lane 1 shows the result of using the nucleotide sequence:

5'TGGTGATGATATCGTGGGTGAGTTCATTTT    V as the diagnostic primer and the oligonucleotide designated I as hereinbefore defined as the amplification primer. The human genomic DNA used was from a normal homozygote having a normal nucleotide (A) present at the potential S mutation point of the human α1 antitrypsin gene. The expected 267 bp amplification product is clearly visible. Lane 2 shows the result of using the nucleotide sequence:

5'TGGTGATGATATCGTGGGTGAGTTCATTTA    VI as the diagnostic primer and the oligonucleotide designated I as hereinbefore defined as the amplification primer. The human genomic DNA used was from a normal homozygote having a normal nucleotide (A) present at the potential S mutation point of the human α1 antitrypsin gene. In the presence of an A—A mismatch no 267 bp amplification product is formed. Lane 3 shows a control band based on the human apolipoprotein B gene the sequences used being

AATGAATTTATCAGCCAAAACTTTTACAGG    XIII and

CTCTGGGAGCACAGTACGAAAAACCACTT    XIV

Lane 4 has been left blank.

Lane 5 shows the result of using the nucleotide sequence

5'CCGTGCATAAGGCTGTGCTGACCATCGACG 3'    VII as a diagnostic primer in Example 4. The diagnostic primer carries the 3' terminal nucleotide (G) capable of base pairing with a normal nucleotide (C) at the potential Z mutation point and is otherwise completely complementary to the sample DNA. The sample DNA used was from a normal homozygote having a normal nucleotide (C) present at the potential Z mutation point of the human α1 antitrypsin gene. Lane 6 shows the result of using the nucleotide sequence:

5'CCGTGCATAAGGCTGTGCTGACCATCGACA 3'    VIII as a diagnostic primer in Example 4. The diagnostic primer carries the 3' terminal nucleotide (A) capable of base pairing with a mutant nucleotide (T) at the Z mutation point but is otherwise completely complementary to the sample DNA. The sample DNA used was from a normal homozygote having a normal nucleotide (C) present at the potential Z mutation point of the human α1 antitrypsin gene. Lane 7 shows the result of using the nucleotide sequence of formula VII as a diagnostic primer in Example 4. The sample DNA used was from a homozygote affected with the human α1 antitrypsin genetic disorder and having a mutant nucleotide (T) at the Z mutation point. Lane 8 shows the result of using the nucleotide sequence of formula VIII as a diagnostic primer in Example 4. The sample DNA used was from a homozygote affected with the human α1 antitrypsin genetic disorder and having a mutant nucleotide (T) at the Z mutation point. The nucleotide sequence of the amplification primer used in each of the tests shown in Lanes 5–8 is of formula IV as hereinbefore defined. It can be seen that production of a 150 bp amplification product is not fully suppressed by the presence of an A–C mismatch (lane 6) and is even less suppressed by the presence of a GT mismatch (lane 7).

Figure 9:
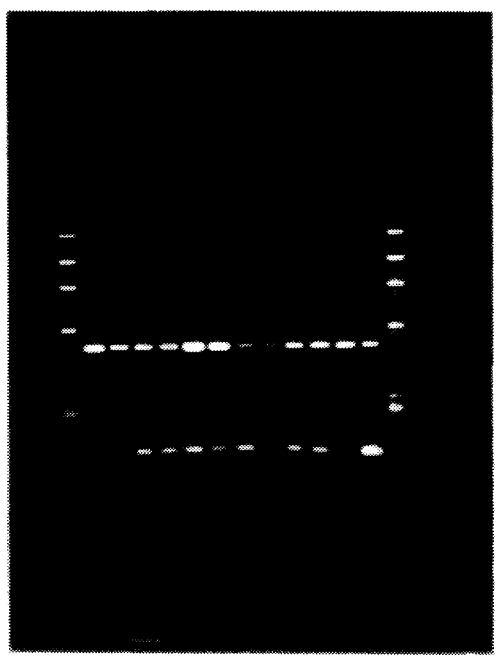
FIG. 9 shows the results of visualisation of the gel obtained in Example 4.

FIG. 9 shows the result of visualisation of the gel obtained in Example 4. Lanes 1 and 14 show the size marker bacteriophage X174 DNA cleaved with Hae III; Lane 2 shows the result of using the nucleotide sequence:

5'CCGTGCATAAGGCTGTGCTGACCATAGACG 3'    IX as a diagnostic primer in the presence of sample DNA having a normal nucleotide (C) present at the potential Z mutation point of the human α1 antitrypsin gene (sample DNA from a normal homozygote). The diagnostic primer carries a deliberate alteration (underlined in sequence IX-A instead of C) in respect of the fifth nucleotide from the 3' terminus but a 3' terminal nucleotide (G) capable of base pairing with a normal nucleotide (C) present at the potential Z mutation point. Lane 3 shows the result of using the nucleotide sequence:

5'CCGTGCATAAGGCTGTGCTGACCATAGACA 3'    X as a diagnostic primer in the presence of sample DNA having a normal nucleotide (C) present at the potential Z mutation point (sample DNA from a normal homozygote). The diagnostic primer carries a deliberate alteration (underlined in sequence X-A instead of C) in respect of the fifth nucleotide from the 3' terminus and a 3' terminal nucleotide (A) capable of base pairing with a mutant nucleotide (T) if present at the potential Z mutation point; Lane 4 shows the result of using the nucleotide sequence IX (as hereinbefore defined) as a diagnostic primer in the presence of sample DNA from a heterozygote for the Z mutation and thus a carrier of the human α1 antitrypsin deficiency genetic disorder; Lane 5 shows the result of using the nucleotide sequence X (as hereinbefore defined) as a diagnostic primer in the presence of sample DNA from a heterozygote for the Z mutation and thus a carrier of the human α1 antitrypsin deficiency genetic disorder. Lane 6 shows the result of using the nucleotide sequence IX (as hereinbefore defined) as a diagnostic primer in the presence of sample DNA from a homozygote affected with the human α1 antitrypsin genetic disorder, Lane 7 shows the result of using the nucleotide sequence X (as hereinbefore defined) as a diagnostic primer in the presence of sample DNA from a homozygote affected with the human α1 antitrypsin genetic disorder.

Lane 8 shows the result of using the nucleotide sequence:

5'CCGTGCATAAGGCTGTGCTGACCATCGCCG 3'    XI as a diagnostic primer in the presence of sample DNA having a normal nucleotide (C) present at the potential Z mutation point of the human α1 antitrypsin gene (sample DNA from a normal homozygote). The diagnostic primer carries a deliberate alteration (underlined in sequence XI-C instead of A) in respect of the third nucleotide from the 3' terminus, but a 3' terminal (G) capable of base pairing with a normal nucleotide (C) present at the potential Z mutation point; Lane 9 shows the result of using the nucleotide sequence;

5' CCGTGCATAAGGCTGTGCTGACCATCGCCA 3'    XII as a diagnostic primer in the presence of sample DNA having a normal nucleotide (C) present at the potential Z mutation point (sample DNA from a normal homozygote). The diagnostic primer carries a deliberate alteration (underlined in sequence XII-C instead of A) in respect of the third nucleotide from the 3' terminus and a 3' terminal nucleotide (A) capable of base pairing with a mutant nucleotide (T) if present at the potential Z mutation point; Lane 10 shows the result of using the nucleotide sequence XI as hereinbefore defined) as a diagnostic primer in the presence of sample DNA from a heterozygote for the Z mutation and thus a carrier of the human α1 antitrypsin deficiency genetic disorder; Lane 11 shows the result of using the nucleotide sequence XII as hereinbefore defined) as a diagnostic primer in the presence of sample DNA from a heterozygote for the Z mutation and thus a carrier of the human α1 antitrypsin genetic disorder. Lane 12 shows the result of using the nucleotide sequence XI (as hereinbefore defined) as a diagnostic primer in the presence of sample DNA from a homozygote affected with the human α1 antitrypsin deficiency genetic disorder. Lane 13 shows the result of using the nucleotide sequence XII (as hereinbefore defined) as a diagnostic primer in the presence of sample DNA from a homozygote affected with the human α1 antitrypsin genetic disorder.

In each of lanes 2–13 the nucleotide sequence of formula IV was used as the amplification primer and the nucleotide sequences of formula XIII:

AATGAATTTATCAGCCAAAACTTTTACAGG    XIII and formula XIV:

CTCTGGGAGCACAGTACGAAAAACCACTT    XIV were used as a control. The bands corresponding to the control are marked (C) in FIG. 9 and correspond to a 510 bp amplification product from exon 26 of the human apolipoprotein B gene.

Figure 10:
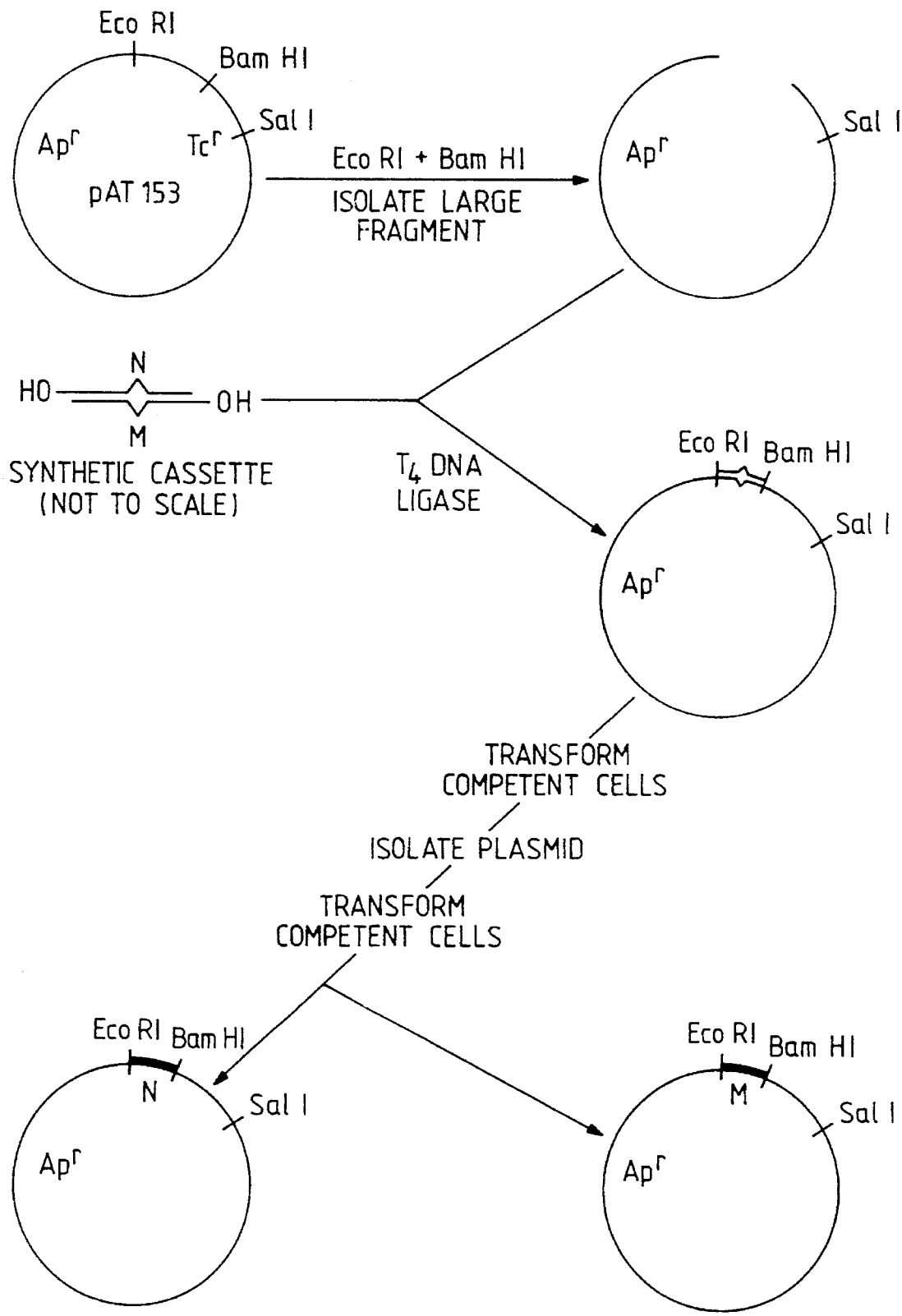
FIG. 10 illustrates the use of a cassette plasmid system to amplify a desired DNA duplex.

FIG. 10 illustrates the use of a cassette plasmid system. The plasmid pAT 153 having regions conferring antibiotic resistance to Ampicillin (Ap$^r$) and Tetracycline (Tc$^r$) as well as having the restriction sites EcoRI, BamHI and SalI is digested with EcoRI and BamHI. The synthetic cassette, comprising a DNA duplex with a mismatched nucleotide (in the centre) due to the presence of both a normal and variant sequence, is ligated using T$_4$ DNA ligase into the plasmid host as shown. The plasmid is then replicated and selected as shown.

The system is illustrated in more detail as follows: Synthetic DNA cassettes were prepared, each comprising two annealed 65 mers having EcoRI and BamHI restriction termini and the middle base pair being mismatched due to a variant nucleotide. These cassettes were introduced into pAT153 plasmid hosts as described above and, after transformation, tetracycline sensitive clones were isolated and plasmid extracted. The plasmid extracts were then used in a secondary transformation to provide clones with either normal or variant inserts. To verify that the clones contained the complete normal or mutant sequence about 2 μg of each was sequenced, after NaOH denaturation, and using T4 DNA polymerase (Sequenase, US Biochemicals) and $^{32}$P end labelled primer. When at least one normal and one variant of each type had been found, a representative clone of each was grown in bulk, the plasmid extracted and cleaned using a CsCl gradient. The cassettes were then digested with SalI, extracted with phenol/chloroform, precipitated and washed with 70% ethanol. The cassettes were then ready to be used, for example in polymerase chain reactions to determine the sensitivity and specificity of the various oligonucleotides.

FIG. 11 illustrates the fifth embodiment (linear amplification) of the invention. In a) a normal genomic DNA sequence is shown together with two diagnostic primers one of which is complementary at its 3' terminal to the normal genomic DNA sequence and the second primer having a nucleotide complementary to the suspected variant nucleotide at its 3' terminal. In b) a variant genomic DNA sequence is shown together with the same two diagnostic primers. When either genomic DNA sequence is contacted with the primers under conditions allowing complementary hybridisation in both cases hybridisation will occur. Addition of all four nucleoside triphosphates under conditions allowing primer extension will only lead to an extended product in the case of a) the normal sequence primer and b) the variant sequence primer, extension of the other primer being prevented by the mismatch. Moreover as shown in c) where only three or fewer appropriate nucleoside triphosphates are added instead of four, extension of the appropriate primer is prevented at a given point by the lack of the appropriate nucleoside triphosphate(s).

FIG. 12 shows the results of visualisation of the gel obtained in Example 5.

Lanes 1 and 2 correspond to DNA for a normal homozygote(MM), lanes 3 and 4 to DNA for a heterozygote(MS) and lanes 5 and 6 to DNA for a variant homozygote(SS). In respect of lanes 1, 3 and 5, oligonucleotide XXII (normal) was used and in respect of lanes 2, 4 and 6 oligonucleotide XXI (variant) was used. As predicted oligonucleotide extension did not occur in respect of lanes 2 or 5. The detected product bands are indicated by chevrons.

FIG. 13 shows the results of visualisation of the gel obtained in Example 6.

The lane on the far left shows size markers used to confirm the sizes of the products obtained. Lanes 1 and 2 correspond to DNA from a normal homozygote(MM), lanes 3 and 4 to DNA from a heterozygote(MZ) and lanes 5 and 6 to DNA from a variant homozygote (ZZ). In respect of lanes 1, 3 and 5 primers XIX and XI were used; for lanes 2, 4 and 6 primers XII and XX were used. As expected primer extension did not occur in respect of lanes 2 or 5. The detected product bands are indicated by chevrons.

Sequence of the α-1-antitrypsin S locus (exon III).

The bases shown in lower case depict the normal sequence of each locus. Underlined bases in the primers show the deliberate mismatch inserted to destabilise the primers. The coordinates are as assigned by Long et al (1984) Biochemistry 23: 4828–4837.

```
5'GCCTGATGAGGGGAAACTACAGCACCTGGT    XXI
5'GCCTGATGAGGGGAAACTACAGCACCTGGA    XXII
5'CTTCCTGCCTGATGAGGGGAAACTACAGCACCTGGa
3'GAAGGACGGACTACTCCCCTTTGATGTCGTGGACCt
                    |
                  7642
```

-continued

```
                                                        7718
                                                         |
aAAATGAACTCACCCACGATATCATCACCAAGTTCCTGGAAA 3'
tTTTACTTGAGTGGGTGCTATAGTAGTGGTTCAAGGACCTTT 5'

TTTTACTTGAGTGGGTGCTATAGTAGTGGT 5'   XXIII
ATTTACTTGAGTGGGTGCTATAGTAGTGGT 5'   XXIV

CACACCTCTTAGCCATGTTGGGACTGAGGCCCATCAGGACTGGC 3'
GTGTGGAGAATCGGTACAACCCTGACTCCGGGTAGTCCTGACCG 5'
                                              |
                                            7811

GTGGAGAATCGGTACAACCCTGACTCCGGG 5'
    TTGGAGAATCGGTACAACCCTGACTCCGGG 5'
```

Sequence of the α-1-antitrypsin Z locus (exon V)

The bases shown in lower case depict the normal sequence of each locus. Underlined bases in the primers show the deliberate mismatch inserted to destabilise the primers.

```
5' CCGTGCATAAGGCTGTGCTGACCCTCGACA   XVI
5' CCGTGCATAAGGCTGTGCTGACCCTCGACG   XV
5' CCGTGCATAAGGCTGTGCTGACCATAGACA   X
5' CCGTGCATAAGGCTGTGCTGACCATAGACG   IX
5' CCGTGCATAAGGCTGTGCTGACCATCGCCA   XII
5' CCGTGCATAAGGCTGTGCTGACCATCGCCG   XI
5' CCGTGCATAAGGCTGTGCTGACCATCGACA   VIII
5' CCGTGCATAAGGCTGTGCTGACCATCGACG   VII

5' TCCAGGCCGTGCATAAGGCTGTGCTGACCATCGACg
3' AGGTCCGGCACGTATTCCGACACGACTGGTAGCTGc
   |
 9954
                                           10030
                                             |
gAGAAAGGGACTGAAGCTGCTGGGGCCATGTTTTTAGAGGCC 3'
cTCTTTCCCTGACTTCGACGACCCCGGTACAAAAATCTCCGG 5'

CTCTTTCCCTGACTTCGACGACCCCGGTAC 5'   XVII
TTCTTTCCCTGACTTCGACGACCCCGGTAC 5'   XVIII
CTCATTCCCTGACTTCGACGACCCCGGTAC 5'   XIX
TTCATTCCCTGACTTCGACGACCCCGGTAC 5'   XX
```

The invention is illustrated, but not limited, by the following Examples. In the Examples unless otherwise stated the materials used are in the following amounts or concentrations:

Substrate DNA: 1 μg human genomic DNA

Oligonucleotides: 100 pmoles of each appropriate oligonucleotide.

Deoxynucleoside triphosphates: Each at 1.5 mM final concentration

Buffer (final concentrations in reaction mixture):

| |
|---|
| 67 mM Tris (pH 8.8 with HCl) |
| 16.6 mM Ammonium sulphate |
| 6.7 mM Magnesium chloride |
| 10 mM β-Mercaptoethanol |
| 6.7 μM EDTA |

Loading buffer: 35% Ficoll 70-(Ficoll 70 is a synthetic polymer made by the copolymerisation of sucrose and epichlorohydrin, the copolymer having an approximate molecular weight average of 70,000—product of Pharmacia) 200 mM Tris-acetate 100 mM Sodium acetate 5 mM EDTA 0.2% Bromophenol blue Size markers:- Bacteriophage φX174 DNA cleaved with Hae III; Size of bands in base pairs is: 1353, 1078, 872, 603, 310, 281, 271, 234, 194, 118 and 72.

EXAMPLE 1

1 μg of human genomic DNA, 100 pmoles of each of the oligonucleotides I, II, III, and IV as hereinbefore defined 1.5 mM (final concentration) of each of the four deoxynucleoside triphosphates and buffer in the final concentrations detailed above were mixed in a 1.5 ml screw cap microcentrifuge tube and the volume adjusted to 100 μl with sterile distilled water. The tube was sealed and placed in a boiling water bath for 5 minutes. The reaction was initiated by adding 1 μl of Taq polymerase containing 1 unit of enzyme (Anglian Biotech batch 3 diluted to 1 unit/μl with the above buffer). The tube was incubated at 58° C. for 4 minutes and then at 91° C. for 2 minutes. The 58° C./91° C. heating/cooling regime was continued for 5 further cycles, at which point 1 further unit of enzyme (as above) was added. The 58° C./91° C. heating/cooling regime was then continued for a further 6 cycles followed by the addition of 1 further unit of enzyme (as above). The above heating/cooling regime was continued for another 6 cycles followed by the addition of 1 further unit of enzyme (as above), then for another 5 cycles followed by the addition of 1 further unit of enzyme (as above), then for a further 2 cycles followed by the addition of 1 further unit of enzyme (as above). This regime was then followed by incubation at 58° C. for 20 minutes.

Detection of the amplification products was effected by combining 15 μl from the reaction mixture with a separate 5 μl gel loading buffer followed by electrophoresis on an agarose gel (3% "NuSieve") containing ethidium bromide (2 μg/ml). Electrophoresis was conducted against size markers to confirm the correct size of the amplification products. The gel was visualised on a transilluminator (300 nm wavelength) and a polaroid photograph taken. Lane 3 of FIG. 7 shows the result of this visualisation. Thus Lane 3 shows amplification of Exon III with primers I and II as hereinbefore defined to generate a 360 bp product and amplification of Exon V with primers III and IV as hereinbefore defined of generate a 220 bp product.

EXAMPLE 2

Example 1 was repeated, but the primer II was replaced by the primer IIa as hereinbefore defined. FIG. 7, Lane 4 shows the result of visualisation of the gel obtained in this Example. It can be seen that no amplification of Exon III has taken place using primers I and IIa as hereinbefore defined, but that amplification of Exon V with primers III and IV as hereinbefore defined has been effected to generate the same 220 bp product as in Example 1.

Example 2 thus demonstrates that a mismatch at the 3' end of an oligonucleotide primer prevents or at least substantially inhibits the initiation of polymerase activity.

EXAMPLE 3

S allele of human α-1-antitrypsin

1 μg of human genomic DNA, 100 pmoles of each of the oligonucleotides detailed below 1.5 mM (final concentration) of each of the four deoxynucleoside triphosphates and buffer in the final concentrations detailed above were mixed in a 1.5 ml screw cap microcentrifuge tube and the volume adjusted to 100 μl with sterile distilled water. The tube was sealed and placed in a boiling water bath for 5 minutes. The reaction was initiated by adding 1 μl of Taq polymerase containing 1 unit of enzyme (Anglian Biotech batch 3 diluted to 1 unit/μl with the above buffer). The tube was incubated at 58° C. for 4 minutes and then at 91° C. for 2 minutes. The 58° C./91° C. heating/cooling regime was continued for 5 further cycles, at which point 1 further unit of enzyme (as above) was added. The 58° C./91° C. heating/cooling regime was then continued for a further 6 cycles followed by the addition of 1 further unit of enzyme (as above). The above heating/cooling regime was continued for another 6 cycles followed by the addition of 1 further unit of enzyme (as above), then for another 5 cycles followed by the addition of 1 further unit of enzyme (as above), then for a further 2 cycles followed by the addition of 1 further unit of enzyme (as above). This regime was then followed by incubation at 58° C. for 20 minutes.

The following tests were conducted on the basis of the above protocol:

a) the oligonucleotides used were

5'TGGTGATGATATCGTGGGTGAGTTCATTTT        V and the oligonucleotide designated I as hereinbefore defined. The human genomic DNA used was from a normal homozygote unaffected by the human α1 antitrypsin genetic disorder; and b) the oligonucleotides used were

TGGTGATGATATCGTGGGTGAGTTCATTTA          VI and the oligonucleotide designated I as hereinbefore defined. The human genomic DNA used was from a normal homozygote unaffected by the human α1 antitrypsin genetic disorder.

Detection of the amplification products was effected by combining 15 μl from the reaction mixture with a separate 5 μl gel loading buffer following the electrophoresis on an agarose gel (3% "NuSieve") containing ethidium bromide (2 μg/ml). Electrophoresis was conducted against size markers (Lane 9 of FIG. 8) to confirm the correct size of the amplification products. The gel was visualised on a transilluminator (300 nm wavelength) and a polaroid photograph taken. Lanes 1 and 2 of FIG. 8 show the result of this visualisation. Thus Lane 1 shows that amplification is effected where the nucleotide sequence of formula V is used having a 3' terminal nucleotide complementary to the corresponding nucleotide at the potential S mutation point in the sample DNA used and a 267 bp amplification product is formed. Lane 2 however shows that no amplification is effected where a mismatch arises at the 3' terminus of the diagnostic primer, the diagnostic primer used having the nucleotide (A) at its 3' terminus which mismatches with the nucleotide(A) in the potential S mutation point of a DNA sample from a normal homozygote.

EXAMPLE 4

Z allele

1 μg of human genomic DNA, 100 pmoles of each of the oligonucleotides detailed below, 1.5 mM (final concentration) of each of the four deoxynucleoside triphosphates and buffer in the final concentrations detailed above were mixed in a 1.5 ml screw cap microcentrifuge tube and the volume adjusted to 100 μl with sterile distilled water. The tube was sealed and placed in a boiling water bath for 5 minutes. The reaction was initiated by adding 1 μl of Taq polymerase containing 0.5 units of enzyme (Anglian Biotech batch 9 diluted to 0.5 units/μl with the above buffer). The tube was incubated at 60° C. for 4 minutes and then at 91° C. for 2 minutes. The 60° C./91° C. heating/cooling regime was continued for 5 further cycles, at which point 0.5 further units of enzyme (as above) was added. The 60° C./91° C. heating/cooling regime was then continued for a further 6 cycles followed by the addition of 0.5 further units of enzyme (as above). The above heating/cooling regime was continued for another 6 cycles followed by the addition of 0.5 further units of enzyme (as above), then for another 5 cycles followed by the addition of 0.5 further units of enzyme (as above), then for a further 3 cycles followed by the addition of 0.5 further units of enzyme (as above). This regime was then followed by incubation at 60° C. for 20 minutes.

The following tests were conducted on the basis of the above protocol:

a) the oligonucleotides used were IX and IV as hereinbefore defined and the human genomic DNA used was from a normal homozygote unaffected by the human α1 antitrypsin genetic disorder;

b) the oligonucleotides used were X and IV as hereinbefore defined and the human genomic DNA used was from a normal homozygote unaffected by the human α1 antitrypsin genetic disorder;

c) the oligonucleotides used were IX and IV as hereinbefore defined and the human genomic DNA used was from a heterozygote for human α1 antitrypsin Z allele;

d) the oligonucleotides used were X and IV as hereinbefore defined and the human genomic DNA used was from a heterozygote for human α1 antitrypsin Z allele;

e) the oligonucleotides used were IX and IV as hereinbefore defined and the human genomic DNA used was from a homozygote (ZZ) affected with the α1 antitrypsin disorder;

f) the oligonucleotides used were X and IV as hereinbefore defined and the human genomic DNA used was from a homozygote (ZZ) affected with the α1 antitrypsin disorder;

g) the oligonucleotides used were XI and IV as hereinbefore defined and the human genomic DNA used was from a normal homozygote unaffected by the human α1 antitrypsin genetic disorder;

h) the oligonucleotides used were XII and IV as hereinbefore defined and the human genomic DNA used was from a normal homozygote unaffected by the human α1 antitrypsin genetic disorder;

i) the oligonucleotides used were XI and IV as hereinbefore defined and the human genomic DNA used was from a heterozygote for human α1 antitrypsin Z allele;

j) the oligonucleotides used were XII and IV as hereinbefore defined and the human genomic DNA used was from a heterozygote for human α1 antitrypsin Z allele;
k) the oligonucleotides used were XI and IV as hereinbefore defined and the human genomic DNA used was from a homozygote (ZZ) affected with the α1 antitrypsin disorder;
l) the oligonucleotides used were XII and IV as hereinbefore defined and the human genomic DNA used was from a homozygote (ZZ) affected with the α1 antitrypsin disorder;

In each test the nucleotide sequences of formula XIII and XIV were used as an amplification control.

Detection of the amplification products was effected by combining 15 µl from the reaction mixture with a separate 5 µl gel loading buffer followed by electrophoresis on a 1.4% agarose gel containing ethidium bromide (0.5 µg/ml). Electrophoresis was conducted against size markers as hereinbefore defined to confirm the correct size of the amplification products. The gel was visualised on a transilluminator (300 nm wavelength) and a polaroid photograph taken. Lanes 2–13 of FIG. 9 show the result of this visualisation, Lanes 1 and 14 representing the bands of size markers. Thus Lanes 2–7 show that destabilisation of the diagnostic primer by alteration of the fifth nucleotide from the 3' terminus is not fully effective to enable the primer to distinguish between a normal and a mutant DNA sample under these reaction conditions. Lanes 8–13 however show that alteration of the third nucleotide from the 3' terminus of the diagnostic primer is effective to enable the primer to discriminate between a normal and a mutant DNA sample and can thus be diagnostic for normal homozygotes, heterozygotes (carriers) or ZZ homozygotes affected with human α1 antitrypsin disorder.

The above experiments of this example have also been conducted using a diagnostic primer in which no additional destabilising nucleotide alterations have been made and in which the seventh nucleotide from the 3' terminus has been altered (A to C) to effect destabilisation. In each case the diagnostic primer was not fully effective to discriminate between a normal and a mutant DNA sample, this fact being illustrated in FIG. 8, Lanes 5–8 in respect of the diagnostic primer having no additional destabilising nucleotide alterations.

EXAMPLE 5

The oligonucleotides XXII (normal) and XXI (variant) were used as primers. In this example the dNTP mixture of A, G and T will give a seven base extended primer on the template before requiring the C nucleotide triphosphate. The Tm for these oligonucleotides was calculated to be 94° C. using the formula Tm=4(G+C) and 2(A+T) but this is believed to be only relevant for oligonucleotides up to 23 mers and so 75° C. was selected in preference.

The oligonucleotides (8 pmole each) were labelled at the 5' terminal hydroxyl group using $d^{32}P$ ATP (Amersham 2 µCi) and $T_4$ polynucleotide kinase (4 units) in an 80 µl reaction volume containing 5-mM tris.Cl pH 7.6, 10mM $MgCl_{12}$, 5 mM DTT, 100 µM spermidine and 100 µM EDTA. The kinase reaction was carried out at 37° C. for 20 minutes, then the labelled oligonucleotides were checked by electrophoresis on a 15% polyacrylamide denaturing gel/8M Urea (Pre-run 1 hour 500 V, Main run 4hours 800 V).

Two plasmids were used, one containing the normal sequence (MM) of the S locus of exon III of the human α1-antitrypsin gene and the other containing the variant sequence corresponding to the variant homozygote (SS). Six tubes were set up, 2 of each possible type of DNA. 1 fmole of the appropriate plasmid was used for the homozygotes but the heterozygote was simulated by using 0.5 fmole of both of the plasmids. A 200 fold excess of labelled oligonucleotide was created in each tube by adding 200 fmoles (2 µl of the labelled solution) of either the normal (XXII) or variant (XXI) oligonucleotide to each DNA type. Each tube contained the 3dNTPs A, G and T (Pharmacia) to a final concentration of 5 mM each in a reaction volume of 20 µl containing 6.7 mM EDTA, 6.7 mM $MgCl_2$, 67 mM Tris HCl pH 8.8, 10 mm mercaptoethanol and 16.6 mM ammonium sulphate. Reaction volumes were trebled i.e. 60 µl used in each case to lessen the effects of evaporation. The tubes were boiled for 5 minutes then kept on ice before 3 units of Taq polymerase (Cetus 1 in 5 dilution with 1.5 mM $MgCl_2$, 50 m KCl, 10 mM Tris pH 8.3 and 0.01% gelatin to give 1 unit/µl) were added to each tube. The tubes were spun at 13000 rpm for 2 minutes and a 2 µl aliquot added to 5 µl of formamide/bromophenol blue dye. The tubes were then left at 75° C. in a waterbath. After 4 hours the tubes were removed, spun for 1 minute at 13000 rpm and another 2 µl aliquot taken and added to 5 µl dye. The tubes were then returned to the waterbath at 75° C. After 6 hours the tubes were removed again and a further 3 units of Taq polymerase added to each tube, spun for one minute at 13,000 rpm and a drop of light mineral oil (Sigma) added to lessen evaporation but no aliquot was removed. The tubes were then left at 75° C. overnight. After 24 hours calculated from the end of the initial centrifugation the tubes were removed from the water bath, spun for 1 minute and the final 2 µl aliquots added to 5 µl dye. All the aliquots were electrophoresed on a pre run (1 hr 500 V) 15% denaturing polyacrylamide gel/8M Urea in 1×TBE buffer (0.089M Tris borate, 0.089 boric acid, 0.002M EDTA) for five and half hours at 880 V. The gels were then autoradiographed overnight at room temperature with no screen on slow photographic film. The results are shown in FIG. 12.

Lanes 1 and 2 correspond to DNA for a normal homozygote(MM), lanes 3 and 4 to DNA for a heterozygote (MS) and lanes 5 and 6 to DNA for a variant homozygote(SS). In respect of lanes 1, 3 and 5, oligonucleotide XXII (normal) was used and in respect of lanes 2, 4 and 6 oligonucleotide XXI (variant) was used. As predicted oligonucleotide extension did not occur in respect of lanes 2 or 5. The detected product bands are indicated by chevrons.

EXAMPLE 6

1 ng of cassette plasmid DNA, 100 pmoles of each of the oligonucleotide primers

TTACTTTCACCAGCGTTTCTGGGTGAGCAA and

TATGCGACTCCCTGCATTAGGAGCAGCCCA, 1.5 mM (final concentration) of each of the four deoxynucleoside triphosphates and buffer in the final concentrations detailed above were mixed in a 1.5 ml screw cap microcentrifuge tube and the volume adjusted to 100 µl with sterile deionised water (Milli-Q). The tube was sealed and placed in a boiling water bath for 5 minutes. The reaction was initiated by adding 2 units of Taq polymerase (Cetus) and the mixture sealed with light mineral oil (Sigma) to prevent evaporation. The tube was incubated at 60° C. for four minutes followed by 90° C. for two minutes. This procedure was repeated for a total of thirty cycles.

60 μl of the reaction mixture was then removed and 60 p moles of either primers XIX and XI (normal) or primers XII and XX (variant) added thereto. 1 unit of Taq polymerase (Cetus) was then added to initiate further reaction. The mixture was incubated at 92° C. for two minutes followed by 60° C. for four minutes. This procedure was repeated for a total of four cycles. Detection of the amplification products was effected by combining 10 μl aliquots from the reaction mixture with a gel loading "buffer" followed by electrophoresis on a 3% agarose gel ("Nu Sieve", FMC Bioproducts) containing 0.5 μg/ml ethidium bromide. The gel was visualised on a transilluminator (300 nm wavelength) and a polaroid photograph taken. The results are shown in FIG. 13. The lane on the far left shows size markers used to confirm the sizes of the products obtained. Lanes 1 and 2 correspond to DNA from a normal homozygote (MM), lanes 3 and 4 to DNA from a heterozygote(MZ) and lanes 5 and 6 to DNA from a variant homozygote(ZZ). In respect of lanes 1, 3 and 5 primers XIX and XI were used; for lanes 2, 4 and 6 primers XII and XX were used. As expected primer extension did not occur in respect of lanes 2 or 5. The detected product bands are indicated by chevrons.

We claim:

1. A method for detecting the presence or absence of at least one variant nucleotide in one or more nucleic acids contained in a test sample from an individual, with reference to a control or controls, which method comprises the following steps:

treating the sample, together or sequentially, with appropriate nucleoside triphosphates, an agent for polymerization of the nucleoside triphosphates, a diagnostic primer for each diagnostic portion of a target base sequence and a corresponding amplification primer under hybridizing conditions, the nucleotide sequence of said diagnostic primer being such that it is substantially complementary to said diagnostic portion, a 31 terminal nucleotide of the diagnostic primer being either complementary to a suspected variant nucleotide or to the corresponding normal nucleotide, whereby an extension product of the diagnostic primer is synthesized when said terminal nucleotide of the diagnostic primer is complementary to the corresponding nucleotide in the target base sequence, no extension product being synthesized when the said terminal nucleotide of the diagnostic primer is not complementary to the corresponding nucleotide in the target base sequence;

any extension product of the diagnostic primer formed being capable of serving as a template for synthesis of an extension product of said amplification primer after separation from its complement;

amplifying any extension product; and detecting the presence or absence of the suspected variant nucleotide from the presence or absence of amplification product obtained as above, with reference to the control or controls.

2. The method as claimed in claim 1 wherein the amplifying step comprises:

(i) treating the sample under denaturing conditions to separate the primer extension product from its template where such extension product is formed;

(ii) contacting single strands produced above, either together or sequentially, with appropriate nucleoside triphosphates, an agent for polymerization of the nucleoside triphosphates, a diagnostic primer and an amplification primer as herein defined whereby, where possible, to synthesize further extension products using the single strands produced above as templates;

(iii) repeating the above steps a sufficient number of times to result in detectable amplification of the appropriate nucleotide sequence.

3. The method as claimed in claim 1 which comprises treating the sample, together or sequentially with either (a) a first diagnostic primer having a sequence substantially complementary to a diagnostic portion of a first nucleic acid sequence, the first diagnostic primer having a terminal nucleotide complementary to said suspected variant nucleotide, and a second diagnostic primer having a sequence substantially complementary to a second diagnostic portion of a second nucleic acid sequence, the second diagnostic primer having a terminal nucleotide complementary to the complementary suspected variant nucleotide; or (b) a first diagnostic primer having a sequence substantially complementary to a diagnostic portion of a first nucleic acid sequence, the first diagnostic primer having a terminal nucleotide complementary to the normal nucleotide which corresponds to said suspected variant nucleotide, and a second diagnostic primer having a sequence substantially complementary to a diagnostic portion of a second nucleic acid sequence, the second diagnostic primer having a terminal nucleotide complementary to the normal nucleotide which corresponds to said suspected variant nucleotide; said terminal nucleotide of the first diagnostic primer and said terminal nucleotide of the second diagnostic primer being at the 3' end of the respective primers and the first nucleic acid sequence being in the opposite sense to the second nucleic acid sequence.

4. A set of two nucleic acids consisting of sequences, each independently of from about 5 to 50 bp, a terminal nucleotide at the 3' end of at least one sequence being complementary to either a suspected variant nucleotide associated with a known genetic disorder or to the corresponding normal nucleotide, the remainder of the sequence being substantially complementary to the corresponding target base sequence adjacent to the suspected variant nucleotide or corresponding normal nucleotide the sequence being such that when used as a diagnostic primer in the method of claim 1 an extension product of the diagnostic primer is synthesized when said terminal nucleotide of the diagnostic primer is complementary to the corresponding nucleotide in the target base sequence, no extension product being synthesized when the said terminal nucleotide of the diagnostic primer is not complementary to the corresponding nucleotide in the target base sequence, and wherein one of the set of two nucleotide sequences is a corresponding amplification primer to a diagnostic primer as defined above.

5. The set as claimed in claim 4 wherein the suspected variant nucleotide results from a point mutation of the corresponding normal sequence.

6. A kit for detecting the presence or absence of at least one or more nucleic acids contained in a sample, which kit comprises:

two diagnostic primers for each diagnostic portion of a target base sequence, a terminal nucleotide at the 3' of one diagnostic primer being complementary to a suspected variant nucleotide associated with a known genetic disorder and a terminal nucleotide at the 3' of the other diagnostic primer being complementary to the corresponding normal nucleotide, such that in use an extension product of the diagnostic primer is synthesized when said terminal nucleotide of the diagnostic primer is complementary to the corresponding nucleotide in the target base sequence, no extension product being synthesized when said terminal nucleotide of the diagnostic primer is not complementary to the corresponding nucleotide in the target base sequence; and (ii) a corresponding amplification primer for the two diagnostic primers.

7. The kit as claimed in claim 6 which further comprises each of four different nucleoside triphosphates and an agent for polymerization of the said nucleoside triphosphates.

8. The kit as claimed in claim 6 which comprises diagnostic primers for more than one diagnostic portion of a target base sequence.

9. The method as claimed in claim 1 wherein the suspected variant nucleotide is associated with an inherited or acquired disease.

10. The method as claimed in claim 1 wherein the test sample comprises genomic DNA.

11. The method as claimed in claim 1 wherein the test sample comprises no more than 1 μg of DNA or RNA.

* * * * *